US009265726B2

(12) United States Patent
Abram et al.

(10) Patent No.: US 9,265,726 B2
(45) **Date of Patent: *Feb. 23, 2016**

(54) FOAMABLE SUSPENSION GEL

(71) Applicant: STIEFEL RESEARCH AUSTRALIA PTY LTD, Rowville, Victoria (AU)

(72) Inventors: Albert Zorko Abram, Wantirna (AU); Lilian Fuchshuber, Narre Warren (AU)

(73) Assignee: STIEFEL RESEARCH AUSTRALIA PTY LTD, Rowville, Victoria (AU)

( * ) Notice: Subject to any disclaimer, the term of this patent is extended or adjusted under 35 U.S.C. 154(b) by 58 days.

This patent is subject to a terminal disclaimer.

(21) Appl. No.: 14/275,108

(22) Filed: May 12, 2014

(65) Prior Publication Data

US 2014/0248220 A1 Sep. 4, 2014

Related U.S. Application Data

(63) Continuation of application No. 13/906,806, filed on May 31, 2013, now Pat. No. 8,758,728, which is a continuation of application No. 13/224,993, filed on Sep. 2, 2011, now Pat. No. 8,475,770, which is a continuation of application No. 11/730,011, filed on Mar. 29, 2007, now Pat. No. 8,158,109.

(60) Provisional application No. 60/744,082, filed on Mar. 31, 2006.

(51) Int. Cl.

| | |
|---|---|
| *A61K 31/7034* | (2006.01) |
| *A61K 9/12* | (2006.01) |
| *A61K 9/00* | (2006.01) |
| *A61K 9/06* | (2006.01) |
| *A61K 31/192* | (2006.01) |
| *A61K 31/203* | (2006.01) |
| *A61K 31/63* | (2006.01) |
| *A61K 47/36* | (2006.01) |
| *A61K 31/327* | (2006.01) |
| *A61K 31/7056* | (2006.01) |

(52) U.S. Cl.

CPC ............... *A61K 9/122* (2013.01); *A61K 9/0014* (2013.01); *A61K 9/06* (2013.01); *A61K 31/192* (2013.01); *A61K 31/203* (2013.01); *A61K 31/327* (2013.01); *A61K 31/63* (2013.01); *A61K 31/7034* (2013.01); *A61K 31/7056* (2013.01); *A61K 47/36* (2013.01); *Y10S 514/945* (2013.01); *Y10S 514/952* (2013.01)

(58) Field of Classification Search

CPC ....... A61K 9/122; A61K 9/0014; A61K 9/06; A61K 31/7034; A61K 2300/00

IPC ................. A61K 9/122, 9/0014, 9/06, 31/7034, A61K 2300/00

See application file for complete search history.

(56) References Cited

U.S. PATENT DOCUMENTS

| | | | |
|---|---|---|---|
| 3,906,108 | A | 9/1975 | Felty |
| 3,952,099 | A | 4/1976 | Smith |
| 3,969,516 | A | 7/1976 | Stoughton |
| 4,387,107 | A | 6/1983 | Klein et al. |
| 4,443,442 | A | 4/1984 | Skillern |
| 4,497,794 | A | 2/1985 | Klein et al. |
| 4,505,896 | A | 3/1985 | Bernstein |
| 4,609,674 | A | 9/1986 | Gupte |
| 4,671,956 | A | 6/1987 | Bouillon et al. |
| 4,692,329 | A | 9/1987 | Klein et al. |
| 4,731,362 | A | 3/1988 | Hamashima et al. |
| 4,803,228 | A | 2/1989 | Jacquet et al. |
| 4,806,262 | A | 2/1989 | Snyder |
| 4,882,182 | A | 11/1989 | Halls et al. |
| 4,906,617 | A | 3/1990 | Jacquet et al. |
| 4,915,934 | A | 4/1990 | Tomlinson |
| 4,960,772 | A | 10/1990 | Sebag et al. |
| 4,981,678 | A | 1/1991 | Tomlinson |
| 5,019,567 | A | 5/1991 | Philippe et al. |
| 5,086,075 | A | 2/1992 | De Villez |
| 5,089,509 | A | 2/1992 | Chandraratna |
| 5,204,093 | A | 4/1993 | Victor |
| 5,254,109 | A | 10/1993 | Smith et al. |
| 5,352,437 | A | 10/1994 | Nakagawa et al. |
| 5,397,564 | A | 3/1995 | Seki et al. |
| 5,446,028 | A | 8/1995 | Klein et al. |
| 5,449,519 | A | 9/1995 | Wolf et al. |
| 5,466,446 | A | 11/1995 | Stiefel et al. |
| 5,470,884 | A | 11/1995 | Corless et al. |
| 5,516,504 | A | 5/1996 | Tomlinson |

(Continued)

FOREIGN PATENT DOCUMENTS

| | | | |
|---|---|---|---|
| EP | 0 331 489 | A2 | 9/1989 |
| WO | 85/01876 | A1 | 5/1985 |
| WO | 86/00196 | A1 | 1/1986 |
| WO | 88/04896 | A1 | 7/1988 |
| WO | 93/15726 | A1 | 8/1993 |
| WO | 93/20796 | A1 | 10/1993 |
| WO | 96/27376 | A1 | 9/1996 |
| WO | 97/17075 | A1 | 5/1997 |
| WO | 99/20250 | A1 | 4/1999 |
| WO | 99/53923 | A1 | 10/1999 |
| WO | 00/15193 | A1 | 3/2000 |
| WO | 03/055472 | A1 | 7/2003 |
| WO | 2007/002831 | A2 | 1/2007 |
| WO | 2007/092312 | A2 | 8/2007 |

OTHER PUBLICATIONS

Abram, et al., Mousses, Chapter 19, pp. 221-232, Soltec Research Pty Ltd., Rowville, Victoria, Australia, Jun. 2001.

(Continued)

*Primary Examiner* — Mina Haghighatian

(74) *Attorney, Agent, or Firm* — Nath, Goldberg & Meyer; Joshua B. Goldberg; Scott H. Blackman

(57) ABSTRACT

The present subject matter provides foamable suspension gels that foam after release from a container. The foamable suspension gels contain at least one pharmaceutically active agent that is sparingly soluble to insoluble in water, a second pharmaceutically active agent, and optionally a third active agent.

19 Claims, 4 Drawing Sheets

(56) References Cited

U.S. PATENT DOCUMENTS 5,562,642 A 10/1996 Smith et al.
5,573,757 A 11/1996 Riess et al.
5,602,130 A 2/1997 Chandraratna
5,621,008 A 4/1997 Ptchelintsev
5,635,469 A 6/1997 Fowler et al.
5,648,389 A 7/1997 Gans et al.
5,660,839 A 8/1997 Allec et al.
5,679,324 A 10/1997 Lisboa et al.
5,690,923 A 11/1997 DeVringer et al.
5,690,946 A 11/1997 Koulbanis et al.
5,707,635 A 1/1998 Deckner et al.
5,716,625 A 2/1998 Hahn et al.
5,721,275 A 2/1998 Bazzano
5,733,886 A 3/1998 Baroody et al.
5,756,107 A 5/1998 Hahn et al.
5,756,119 A 5/1998 Deckner et al.
5,767,098 A 6/1998 Klein et al.
5,776,430 A 7/1998 Osborne et al.
5,783,202 A 7/1998 Tomlinson et al.
5,788,155 A 8/1998 Martin et al.
5,811,088 A 9/1998 Hunter et al.
5,843,881 A 12/1998 Dubois et al.
5,879,688 A 3/1999 Coury et al.
5,894,019 A 4/1999 Hesse et al.
5,914,334 A 6/1999 Charu
5,935,554 A 8/1999 Tomlinson
5,948,416 A 9/1999 Wagner et al.
5,958,436 A 9/1999 Hahn et al.
5,976,565 A 11/1999 Fotinos
5,985,300 A 11/1999 Crotty et al.
5,993,787 A 11/1999 Sun et al.
5,997,885 A 12/1999 Koulbanis et al.
5,998,392 A 12/1999 Simard et al.
6,001,380 A 12/1999 Smith et al.
6,013,637 A 1/2000 Klein et al.
6,017,549 A 1/2000 Knight et al.
6,017,938 A 1/2000 Bershad
6,048,902 A 4/2000 Lebwohl et al.
6,083,962 A 7/2000 Rose et al.
6,096,765 A 8/2000 Bershad
6,117,843 A 9/2000 Barody et al.
6,139,850 A 10/2000 Hahn et al.
6,193,956 B1 2/2001 Liu et al.
6,211,250 B1 4/2001 Tomlinson et al.
6,231,875 B1 5/2001 Sun et al.
6,267,949 B1 7/2001 Halls
6,280,764 B1 8/2001 Fotinos
6,284,234 B1 9/2001 Niemiec et al.
6,383,471 B1 5/2002 Chen et al.
6,387,383 B1 5/2002 Dow et al.
6,419,913 B1 7/2002 Niemiec et al.
6,428,772 B1 8/2002 Singh et al.
6,448,233 B1 9/2002 Lefevre et al.
6,462,025 B2 10/2002 Vishnupad
6,495,158 B1 12/2002 Buseman et al.
6,495,498 B2 12/2002 Niemiec et al.
6,517,847 B2 2/2003 Dow et al.
6,524,594 B1 2/2003 Santora et al.
6,730,308 B1 5/2004 Sefton
6,735,470 B2 5/2004 Henley et al.
6,762,158 B2 7/2004 Lukenbach et al.
6,774,100 B2 8/2004 Vishnupad
6,911,211 B2 6/2005 Eini et al.
7,141,237 B2 11/2006 Abram et al.
7,374,747 B2 5/2008 Abram et al.
7,749,488 B2 7/2010 Abram et al.
8,158,109 B2 4/2012 Abram et al.
8,475,770 B2 7/2013 Abram et al.
8,758,728 B2 * 6/2014 Abram ................. A61K 9/0014
424/45
2002/0035046 A1 3/2002 Lukenbach et al.
2002/0035070 A1 3/2002 Gardlik et al.
2002/0058010 A1 5/2002 Picard-Lesboueyries et al.
2002/0064541 A1 5/2002 Lapidot et al.
2002/0119174 A1 8/2002 Gardlik et al.
2002/0193321 A1 12/2002 Vishnupad et al.
2003/0004118 A1 1/2003 Vishnupad et al.
2003/0018295 A1 1/2003 Henley et al.
2003/0031690 A1 2/2003 Kang et al.
2003/0044432 A1 3/2003 Manetta et al.
2003/0064097 A1 4/2003 Patel et al.
2003/0077301 A1 4/2003 Maibach et al.
2003/0078172 A1 4/2003 Guiramand et al.
2003/0104041 A1 6/2003 Hsu et al.
2003/0118511 A1 6/2003 Jones et al.
2003/0138503 A1 7/2003 Staniforth et al.
2003/0170196 A1 9/2003 Orsoni et al.
2003/0215493 A1 11/2003 Patel
2004/0043946 A1 3/2004 Popp
2004/0101566 A1 5/2004 Cooper et al.
2004/0151671 A1 8/2004 Abram et al.
2004/0156873 A1 8/2004 Gupta
2004/0157766 A1 8/2004 Embil et al.
2004/0167046 A1 8/2004 Lukenbach et al.
2004/0167223 A1 8/2004 Popp
2004/0170659 A1 9/2004 Bhagwat et al.
2004/0171561 A1 9/2004 Popp
2004/0176737 A1 9/2004 Henley et al.
2004/0202725 A1 10/2004 Dascalu
2004/0241099 A1 12/2004 Popp et al.
2004/0265240 A1 12/2004 Tamarkin et al.
2005/0009717 A1 1/2005 Lukenbach et al.
2005/0014729 A1 1/2005 Pulaski
2005/0031547 A1 2/2005 Tamarkin et al.
2005/0054991 A1 3/2005 Tobyn et al.
2005/0069566 A1 3/2005 Tamarkin et al.
2005/0074414 A1 4/2005 Tamarkin et al.
2005/0075407 A1 4/2005 Tamarkin et al.
2005/0186147 A1 8/2005 Tamarkin et al.
2005/0255048 A1 11/2005 Hirsh et al.
2005/0271598 A1 12/2005 Friedman et al.
2005/0276865 A1 12/2005 Buyuktimkin et al.
2006/0140984 A1 6/2006 Tamarkin et al.
2006/0193789 A1 8/2006 Tamarkin et al.
2006/0198803 A1 9/2006 Giniger
2008/0031907 A1 2/2008 Tamarkin et al.

OTHER PUBLICATIONS

Woodford, et al., "Bioavailability and activity of topical corticosteroids from a novel drug delivery system, the aerosol quick-break foam," J. Pharm. Sci., Jan; vol. 66, No. 1, pp. 99-103, (1977).

Zouboulis, et al., "A multicentre, single-blind, randomized comparison of a fixed clindamycin phosphate/tretinoin gel formulation (Velc®) applied once daily and a clindamycin lotion formulation (Dalacin T®) applied twice daily in the topical treatment of acne vulgaris," British Journal of Dermatology, vol. 143, pp. 498-505, (2000).

Cambazard, "Clinical efficacy of Velac®, a new tretinoin and clindamycin phosphate gel in acne vulgaris," J. Euro. Acad. of Derm. and Vener., 11 (1998), S20-S27.

Van Hoogdalem, "Transdermal absorption of topical anti-acne agents in man: review of clinical pharmacokinetic data," J. Euro. Acad. of Derm. and Vener., 11 (1998), S13-S19.

Richter, et al., "Efficacy of the fixed 1.2% clindamycin phosphate, 0.025% tretinoin gel formulation (Velac®) and a proprietary 0.025% tretinoin gel formulation (Aberela®) in the topical control of facial acne," J. Euro. Acad. of Derm. and Vener., 11 (1998), pp. 227-233.

Richter, et al., "Efficacy of a fixed clindamycin phosphate 1.2%, tretinoin 0.025% gel formulation (Velac) in the topical control of facial acne," J. of Dermatological Treatment, 9, (1998), pp. 81-90.

Rietschel, "Topical Tretinoin in Combination with Topical Clindamycin in the Treatment of Acne," Fitzpatrick's Journal of Clinical Dermatology, Sep. 1994 Supplement.

Connetics Corporation Announces Positive Results from Velac Phase III Pivotal Trials. Published Mar. 24, 2004. Obtained from http://www.biospace.com/news_story.aspx?NewsEntityId=15531420.

Langer, et al., "Treatment of Acne Vulgaris," AFP Clinical Pharmacology, (1979), 20(2), pp. 117-118.

Gloor, et al., "Topical Treatment of acne vulgaris with erythromycin and benzoylperoxide" (Abstract), Z. Hautkr., (1992), 57(12), pp. 867-868.

(56) References Cited

OTHER PUBLICATIONS

Tucker, et al., "Comparison of topical clindamycin phosphate, benzoyl peroxide, and a combination of the two for the treatment of acne vulgaris," (Abstract), Br. J. Dermatol., (1984), 110(4), pp. 487-492.
Gerny, "Experiences in dermatologic practice with combined external treatment of acne with benzoyl peroxide and erythromycin," (abstract), Z. Hautkr., (1984), 59(13), pp. 888-893.
Marsden, "Evidence that method of use, dose and duration of treatment with benzoyl peroxide and tetracycline determined response of acne," (Abstract), J. R. Soc. Med., (1985), 78 Suppl. 10, pp. 25-28.
Norris, et al., "A comparison of the effectiveness of topical tetracycline, benzoyl-peroxide gel and oral tetracycline in the treatment of acne," (Abstract), Clin. Exp. Dermatol., (1991), 16(1), pp. 31-33.
Lookingbill, et al., "Treatment of Acne with a combination clindamycin/benzoyl peroxide gel compared with a clindamycin gel, benzoyl peroxide gel and vehicle gel: Combined results of two double-blind investigations," J. Am. Acad. Dermatol., (1997), 37(4), pp. 590-595.
Leyden, et al., "The Combination Formulation of Clindamycin 1% plus Benzoyl Peroxide 5% versus 3 Different Formulations of Topical Clindamycin Alone in the Reduction of Propionibacterium acnes," Am. J. Clin. Dermatol., (2001), 2(4), pp. 263-266.
Leyden, "Current issues in antimicrobial therapy for the treatment of acne," J. Eur. Acad. Dermatol. Venerol., (2001), 15 (Suppl. 3), pp. 51-55.
Levy, "Dermatopharmacology of a New Combination Gel Formulation for the Topical Treatment of Acne," CUTIS, (2001), 67, pp. 8-12.
Benzaclin TM Topical Gel Prescribing Information, Feb. 2002.
Extended European Search Report; application No. 10159385.3-1219; mailed Jun. 10, 2010.
Aaserud, E., "A Randomized, Double-Blind, Contralateral Study with Water-Based Versus Alcohol-Based Benzoyl Peroxide in the Treatment of Acne Vulgaris," Applicant Internal Study for Benzoyl Peroxide, 12 pages (1988).

* cited by examiner

*Fig. 1*

| | | pH 5 stored @ 5°C | | | | | |
|---|---|---|---|---|---|---|---|
| Time point | INITIAL | 1 MONTH | 2 MONTHS | 3 MONTHS | 6 MONTHS | 9 MONTHS | 12 MONTHS |
| Benzoyl Peroxide (BPO) Content %w/w | 4.98 | 4.98 | 4.95 | 4.99 | 4.90 | 5.05 | 5.08 |
| % BPO remaining compared to initial Content | 100.00 | 100.00 | 99.40 | 100.20 | 98.39 | 101.41 | 102.00 |
| Clindamycin (Clindamycin Phosphate + Clindamycin) Content %w/w | 1.044 | 1.039 | 1.045 | 1.047 | 1.044 | 1.037 | 1.028 |
| % Total Clindamycin remaining compared to initial Content | 100.00 | 99.52 | 100.10 | 100.29 | 100.00 | 99.33 | 98.47 |

FIG. 2

| | | pH 5 stored @ 25°C | | | |
|---|---|---|---|---|---|
| Time point | INITIAL | 1 MONTH | 2 MONTHS | 3 MONTHS | 6 MONTHS |
| Benzoyl Peroxide (BPO) Content %w/w | 4.98 | 4.97 | 4.90 | 4.96 | 4.87 |
| % BPO remaining compared to initial Content | 100.00 | 99.80 | 98.39 | 99.60 | 97.79 |
| % BPO remaining compared to 5°C sample | 100.00 | 99.80 | 98.99 | 99.40 | 99.39 |
| Clindamycin (Clindamycin Phosphate + Clindamycin) Content %w/w | 1.044 | 1.027 | 1.018 | 0.993 | 0.936 |
| % Clindamycin remaining compared to initial Content | 100.00 | 98.37 | 97.51 | 95.11 | 89.66 |

*FIG. 3*

| | | pH 4.5 stored @ 5°C | | | | | |
|---|---|---|---|---|---|---|---|
| Time point | INITIAL | 1 MONTH | 2 MONTHS | 3 MONTHS | 6 MONTHS | 9 MONTHS | 12 MONTHS |
| Benzoyl Peroxide (BPO) Content %w/w | 4.97 | 4.93 | N/A | 4.94 | 4.81 | 4.91 | 4.98 |
| % BPO remaining compared to initial Content | 100.00 | 99.20 | N/A | 99.40 | 96.78 | 98.79 | 100.20 |
| Clindamycin (Clindamycin Phosphate + Clindamycin) Content %w/w | 1.037 | 1.035 | 1.037 | 1.045 | 1.041 | 1.034 | 1.023 |
| % Total Clindamycin remaining compared to initial Content | 100.00 | 99.81 | 100.00 | 100.77 | 100.39 | 99.71 | 98.65 |

*FIG. 4*

| | | **pH 4.5 stored @ 25°C** | | | |
|---|---|---|---|---|---|
| Time point | INITIAL | 1 MONTH | 2 MONTHS | 3 MONTHS | 6 MONTHS |
| Benzoyl Peroxide (BPO) Content %w/w | 4.97 | 4.75 | 4.86 | 4.87 | 4.83 |
| % BPO remaining compared to initial Content | 100.00 | 95.57 | 97.79 | 97.99 | 97.18 |
| % BPO remaining compared to 5°C sample | 100.00 | 96.35 | N/A | 98.58 | 100.42 |
| Clindamycin (Clindamycin Phosphate + Clindamycin) Content %w/w | 1.037 | 1.027 | 1.012 | 0.992 | 0.941 |
| % Clindamycin remaining compared to initial Content | 100.00 | 99.04 | 97.59 | 95.66 | 90.74 |

FOAMABLE SUSPENSION GEL

This application is a Continuation Application of U.S. patent application Ser. No. 13/906,806 filed May 31, 2013, which is a Continuation Application of U.S. patent application Ser. No. 13/224,993, filed Sep. 2, 2011, now U.S. Pat. No. 8,475,770, which is a continuation of U.S. patent. application Ser. No. 11/730,111, filed Mar. 29, 2007 now U.S. Pat. No. 8,158,109, which claims priority to U.S. Provisional application No. 60/744,082 filed Mar. 31, 2006, the contents of each is hereby incorporated by reference in its entirety.

FIELD OF THE INVENTION

The present subject matter relates to topical delivery of at least one active agent that is sparingly soluble to insoluble in water, particularly benzoyl peroxide, in an aqueous, foamable suspension gel.

BACKGROUND OF THE INVENTION

There are many challenges in the topical application of pharmaceutically active agents. One major objective is to achieve percutaneous delivery of the active agent to the site of treatment. The composition should also have desirable cosmetic characteristics. Application should be easy and should not leave a noticeable residue on the surface of the skin. Moreover, the composition should not cause irritation, discomfort, or inconvenience.

Many antifungal and antibacterial agents are used topically to treat epidermal infections. Some antibiotics, such as tetracycline and clindamycin, are also used to treat acne and other skin diseases that are caused, directly or indirectly, by bacteria. One of the side-effects of systemically administered clindamycin is colitis, which can be dangerous and even fatal. Thus, in treating acne, it is desirable to administer clindamycin topically. Cleocin T®, manufactured by Pharmacia-Upjohn, contains clindamycin phosphate, which is inactive in vitro, but is hydrolyzed in vivo to the antibacterially active clindamycin. Cleocin T® is currently available as a gel, a lotion, and a topical solution, and is used for topical treatment of acne vulgaris.

Others have produced topical formulations containing a pharmaceutically active agent that is sparingly soluble to insoluble in water (e.g., benzoyl peroxide) and a second pharmaceutically active agent (e.g., clindamycin). For example, BenzaClin®, manufactured by Dermik Laboratories, and Duac®, manufactured by Stiefel Laboratories, each contain benzoyl peroxide and clindamycin. BenzaClin® and Duac® are currently available as topical gels. Others have described a suspension foam containing benzoyl peroxide and clindamycin, but the foam contains oil and requires a surfactant in addition to a dispersing emulsifier. See, U.S. Patent Publication 2005/0186147.

Lotion, gels and oil-based foams have the disadvantage of extended rub-in and may leave oily residues. The oil can also exacerbate acne. The solution form readily runs off the site of application, and therefore it is difficult to apply controlled amounts using the solution form.

The present subject matter provides a composition having at least one pharmaceutically active compound, which is useful for topical administration as described herein, as a foamable suspension gel that is non-runny, easy to apply, and does not leave a noticeable residue. The present foamable gel composition provides good control of the application of a small amount of product to the desired area.

SUMMARY OF THE INVENTION

The present subject matter provides an aqueous foamable suspension gel for the topical administration of at least one active ingredient that is sparingly soluble to insoluble in water. Thus, according to an aspect of the present subject matter, there is provided up to 40% w/w, for example, 0.5-40%, 1-20%, 2-10%, 0.5%, 1%, 2%, 3%, 4%, 5%, 10%, 15%, 20%, 25%, 30%, 35%, or 40%, of a first active agent that is sparingly soluble to insoluble in water, suspended in an aqueous phase and from about 0.1 to about 2%, for example, 0.1%, 0.2%, 0.5%, 1.0%, 1.5%, or 2.0%, of one or more thickening agents, wherein the gel is aqueous and forms a homogeneous foam.

The present subject matter also provides aqueous, foamable suspension gels for the topical administration of a first active ingredient that is sparingly soluble to insoluble in water and a second active ingredient.

Accordingly, in another aspect, the present subject matter provides an aqueous, foamable suspension gel, comprising or consisting of:

up to 40% w/w, for example, 0.5-40%, 1-20%, 2-10%, 0.5%, 1%, 2%, 3%, 4%, 5%, 10%, 15%, 20%, 25%, 30%, 35%, or 40%, of a first active agent that is sparingly soluble to insoluble in water, suspended in an aqueous phase;

up to 40% w/w, for example, 0.1%-10%, 5-40%, 0.1%, 0.2%, 0.5%, 1%, 2%, 3%, 4%, 5%, 6%, 7%, 8%, 9%, 10%, 11%, 12%, 13%, 14%, 15%, 20%, 25%, 30%, 35%, or 40%, of a second active agent;

from about 0.1% to about 2%, for example, 0.1%, 0.2%, 0.5%, 1.0%, 1.5%, or 2.0%, of one or more thickening agents;

wherein the gel is aqueous and forms a homogenous foam.

In a further aspect, the present subject matter provides an aqueous, foamable suspension gel, comprising or consisting of:

up to 40% w/w, for example, 0.5-40%, 1-20%, 2-10%, 0.5%, 1%, 2%, 3%, 4%, 5%, 10%, 15%, 20%, 25%, 30%, 35%, or 40%, of a first active agent that is sparingly soluble to insoluble in water, suspended in an aqueous phase;

up to 40% w/w, for example, 0.1%-10%, 5-40%, 0.1%, 0.2%, 0.5%, 1%, 2%, 3%, 4%, 5%, 6%, 7%, 8%, 9%, 10%, 11%, 12%, 13%, 14%, 15%, 20%, 25%, 30%, 35%, or 40%, of a second active agent;

from about 0.1% to about 2%, for example, 0.1%, 0.2%, 0.5%, 1.0%, 1.5%, or 2.0%, of a thickening agent;

wherein the gel is aqueous, and has a viscosity of less than about 20,000 centipoises (cP), and forms a homogenous foam.

In another aspect, the present subject matter provides an aqueous, foamable suspension gel, comprising or consisting of:

from about 1% to about 8% w/w benzoyl peroxide suspended in an aqueous phase;

from about 0.025% to about 2% w/w of a retinoid; and from about 0.5% to about 2% xanthan gum;

wherein the gel is aqueous and forms a homogenous foam.

In a further aspect, the present subject matter provides an aqueous, foamable suspension gel, comprising or consisting of:

from about 1% to about 25% w/w benzoyl peroxide as the sole active ingredient present suspended in an aqueous phase; and from about 0.5% to about 2% xanthan gum;

wherein the gel is aqueous and forms a homogenous foam.

In yet another aspect, the present subject matter provides an aqueous, foamable suspension gel, comprising or consisting of:

from about 1% to about 8% w/w of a first active ingredient comprising benzoyl peroxide suspended in an aqueous phase;

from about 0.5% to about 4% w/w of a second active ingredient comprising a retinoid in combination with clindamycin phosphate; and from about 0.5% to about 2% xanthan gum;

wherein the gel is aqueous and forms a homogenous foam.

In some embodiments, the foamable suspension gel is alcohol-free. In some embodiments, the gel is a post-foaming gel that foams after release from a container, for example, a pump or pressurized container.

In another aspect, the present subject matter provides methods for treating a dermatological condition. A method for treating a dermatological condition can comprise or consist of contacting the skin of an individual in need thereof with a foamable suspension gel according to the present subject matter. In some embodiments, the methods provide for the percutaneous treatment of acne.

In an embodiment, the present foamable suspension gel comprises or consists of up to 40% w/w of a first active agent that is sparingly soluble to insoluble in water, suspended in an aqueous phase and selected from the group consisting of benzoyl peroxide, a retinoid, an azole antimicrobial agent, and mixtures thereof; up to 40% w/w of a second active agent selected from the group consisting of an antibacterial, an antifungal, an antibiotic, an immunomodulator, a peptide, a vitamin, a vitamin derivative, an azole, an oxide, and mixtures thereof; wherein if the first active agent is benzoyl peroxide and the second active agent is an antibiotic, then the foamable suspension gel comprises an additional active ingredient.

In a still further embodiment, the first active agent is benzoyl peroxide and the second active agent is sodium sulfacetamide. In a further embodiment of the present subject matter, the first active agent is an azole antimicrobial agent and the second active agent is salicylic acid. In another embodiment, the first active agent is precipitated sulfur and the second active agent is sodium sulfacetamide.

In another embodiment, the foamable suspension gel can comprise benzoyl peroxide as the sole active ingredient. In some embodiments, the present foamable suspension gel can comprise or consist of a first active agent that is sparingly soluble to insoluble in water, suspended in an aqueous phase; optionally a second active agent; optionally a third active agent; one or more thickening agents; and optionally one or more excipients, for example, selected from the group consisting of a dispersing/wetting agent, a pH-adjusting agent, a surfactant, a sunfilter, a propellent, an antioxidant, an additional foaming agent, a chelating/sequestering agent, a solvent, a fragrance, a coloring agent, a preservative, wherein the gel is aqueous and forms a homogenous foam.

In a further aspect, the present subject matter provides methods of producing aqueous, foamable suspension gels, the method can comprise or consist of the following steps in any order:

suspending a first active agent in an aqueous phase, wherein the first active agent is sparingly soluble to insoluble in water, thereby forming a suspension;

increasing the viscosity of the suspension by adding a sufficient amount of a thickening agent to hold the first active agent in a suspension;

adding a second active agent, and wherein the final viscosity of the foamable suspension gel is less than about 40,000 cP. The foamable suspension gel can contain alcohol or be alcohol-free.

In a further aspect, the present subject matter provides an aqueous, foamable suspension gel, that can comprise or consist of:

from about 1% to about 10% w/w benzoyl peroxide, suspended in an aqueous phase;

from about 0.5% to about 2% clindamycin phosphate;

from about 1% to about 2% xanthan gum;

wherein the gel is aqueous, and forms a homogenous foam.

In a still further aspect, the present subject matter provides an aqueous foamable suspension gel, that can comprise or consist of:

from about 4% to about 8% w/w benzoyl peroxide as the sole active ingredient present suspended in an aqueous phase;

from about 0.5% to about 2% xanthan gum;

wherein the gel is aqueous and forms a homogenous foam.

In another embodiment, the present subject matter provides an aqueous foamable suspension gel, that can comprise or consist of:

from about 1% to about 8% w/w of a first active ingredient comprising benzoyl peroxide suspended in an aqueous phase;

from about 0.5% to about 4% of a second active ingredient comprising a retinoid in combination with clindamycin phosphate;

from about 0.5% to about 2% xanthan gum;

wherein the gel is aqueous and forms a homogenous foam.

In a further aspect, the present subject matter provides an aqueous, foamable suspension gel, that can comprise or consist of:

from about 4% to about 8% w/w benzoyl peroxide, suspended in an aqueous phase;

from about 0.025% to about 2% of a retinoid;

from about 0.5% to about 2% xanthan gum;

wherein the gel is aqueous, and forms a homogenous foam.

The embodiments of the further compositions and methods are as described above and in the detailed embodiments, below.

BRIEF DESCRIPTION OF THE FIGURES

FIG. 1 illustrates stability data of an exemplified foamable suspension gel containing benzoyl peroxide and clindamycin having a pH of 5.0 and stored at 5° C.

FIG. 2 illustrates stability data of an exemplified foamable suspension gel containing benzoyl peroxide and clindamycin having a pH of 5.0 and stored at 25° C.

FIG. 3 illustrates stability data of an exemplified foamable suspension gel containing benzoyl peroxide and clindamycin having a pH of 4.5 and stored at 5° C.

FIG. 4 illustrates stability data of an exemplified foamable suspension gel containing benzoyl peroxide and clindamycin having a pH of 4.5 and stored at 25° C.

DETAILED DESCRIPTION OF THE INVENTION

Definitions

Unless the context requires otherwise, the terms “active agent”, “active compound,” “at least one pharmaceutically active compound” and “pharmaceutically active agent” are used interchangeably herein and refer to a substance having a pharmaceutical, pharmacological or therapeutic effect.

As used herein, the terms "administering", "administration", and like terms refer to any method which, in sound medical or cosmetic practice, delivers the composition to a subject in such a manner as to provide a net positive effect.

The terms "antibiotic" and "antibacterial" are used herein interchangeably to refer to a compound that inhibits the growth of, inhibits the virulence of, or kills bacterial cells. The term "antimicrobial" as used herein refers to a substance that kills or inhibits the growth of microbes such as bacteria (antibacterial), fungi (antifungal), viruses (antiviral) or parasites (anti-parasitic) Antibiotics include, e.g., substances produced by various species of microorganisms (e.g., bacteria, fungi, and actinomycetes), variants thereof, and synthetic antibacterial agents. Those of skill in the art are aware of the multitude of antibiotics that can be used in the present subject matter. See, e.g., Chapter 47 of *Goodman & Gilman's The Pharmacological Basis of Therapeutics*, Hardman and Limbard eds., 2001, McGraw-Hill; and *Goodman & Gilman's The Pharmacological Basis of Therapeutics*, Goodman, et al., eds., 2005, and Kucers, et al., *The Use of Antibiotics: A Clinical Review of Antibacterial, Antifungal, and Antiviral Drugs*, Oxford Univ. Press (1997).

The term "lincomycin antibiotic" as used herein refers to an antibiotic originally recovered from *Streptomyces lincolnensis*. Exemplary antibiotics include lincomycin and clindamycin and their pharmaceutically acceptable salts and esters, including hydrochlorides and phosphates. The lincomycin antibiotics are described, for example, in U.S. Pat. Nos. 3,475,407; 3,509,127; 3,544,551 and 3,513,155.

The term "dispersing agent" as used herein refers to a surface-active agent added to a suspending medium to promote uniform and maximum separation of extremely fine solid particles, often of colloidal size. See, Lewis, *Hawley's Condensed Chemical Dictionary,* 14$^{th}$ Edition, 2002. A dispersing agent can also be expressed in terms of its hydrophile-lipophile balance (HLB) number. Similarly, the term "wetting agent" as used herein refers to a surface-active agent that, when added to water, causes it to penetrate more easily into, or to spread over the surface of, another material by reducing the surface tension of the water. See, Lewis, *Hawley's Condensed Chemical Dictionary,* 14$^{th}$ Edition, 2002. A wetting agent can also be expressed in terms of its HLB number. As contemplated herein, a single surface-active agent could potentially have activity as any or all of a surfactant, a dispersing agent, and a wetting agent.

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a net positive effect upon administration. A therapeutically effective amount of the pharmaceutically active agent will cause a substantial relief of symptoms when administered repeatedly over time. Effective amounts of the pharmaceutically active agent will vary with the particular condition or conditions being treated, the severity of the condition, the duration of the treatment, the specific components of the composition being used, and like factors.

The term "foamable" as used herein refers to the composition being able to form a foam. It can be worked or lathered into a foam, for example following application to wet or dry skin. It can form a foam when dispensed from a device that allows air or vapor to be entrapped within the gel during dispensing, for example, an air aspirated foaming dispenser. It can form a foam when dispensed from an aerosol container, for example, wherein a liquefied propellant mixed with the suspension gel facilitates the production of the foam.

As used herein, "homogeneous" or "homogenous" refer to substantially uniform throughout, i.e., a uniform mixture.

The term "pH" as used herein refers to the value given by a suitable, properly standardized, potentiometric instrument (pH meter) capable of reproducing pH values to 0.02 pH units using an indicator electrode sensitive to hydrogen-ion activity, a glass electrode, and a suitable reference electrode. Where approximate pH values suffice, alternate electrodes, pH indicators and/or test papers can be used.

As used herein, the phrase "Pharmaceutically acceptable salt" of an active compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth metal ion, or an aluminum ion; or (3) coordinates with an organic base such as ethanolamine, diethanolamine, triethanolamine, tromethamine, N-methylglucamine, and the like.

As used herein, the term "prodrug" refers to any compound which releases an active agent in vivo when such prodrug is administered to a subject. Prodrugs of an active agent are prepared by modifying one or more functional group(s) present in the active agent in such a way that the modification(s) may be cleaved in vivo to release the parent compound. Prodrugs include compounds wherein a hydroxy, amino or sulfhydryl group in the active agent is bonded to any group, e.g., protecting group, that may be cleaved in vivo to regenerate the free hydroxyl, amino or sulfhydryl group, respectively. Examples of prodrugs include, but are not limited to, active agents whose functional group(s) are protected by one or more protecting groups listed in T. W. Greene and P. G. M. Wuts, *Protective Groups in Organic Synthesis,* 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups which are useful in preparing prodrugs include acyl groups (e.g., formyl, acetyl and trifluoroacetyl), alkyl ethers, phosphate ethers, phosphate esters, and the like. Representative amino protecting groups that are useful in preparing prodrugs include acyl groups (e.g., formyl, acetyl, and trifluoroacetyl), benzyloxycarbonyl (CBZ), tert-butoxycarbonyl (Boc), and the like.

The term "solubility" or "soluble" as used herein refers to the amount of a substance (e.g. a solid) that will dissolve in another substance (e.g., a liquid). Solubility is generally determined at temperatures between 15° C. and 25° C. and expressed as w/v. As used herein, solubility ranges of solute in liquid are as follows:

| | |
|---|---|
| very soluble | 1 in less than 1 |
| freely soluble | 1 in 1 to 1 in 10 |
| soluble | 1 in 10 to 1 in 30 |
| sparingly soluble | 1 in 30 to 1 in 100 |
| slightly soluble | 1 in 100 to 1 in 1000 |
| very slightly soluble | 1 in 1000 to 1 in 10,000 |
| practically insoluble or insoluble | 1 in more than 10,000 |

Solubility ranges are available in published pharmacopoeias, including United States Pharmacopoeia (USP), European Pharmacopoeia (EP), British Pharmacopoeia (BP); and in *Martindale: The Complete Drug Reference*, Sweetman, 2004, Pharmaceutical Press, and in Martindale, *Martindale: The Extra Pharmacopoeia,* 31st Edition, 1996, Amer Pharmaceutical Assn, which is herein incorporated by reference.

The term "treating" as used herein refers to the process of producing an effect on biological activity, function, health, or condition of an organism in which such activity is maintained, enhanced, diminished, or applied in a manner consistent with the general health and well-being of the organism.

The term "vehicle" as used herein refers to a composition which has only excipient or components required to carry an active agent, but which itself has no pharmaceutical or therapeutic effect.

Other terms as used herein are meant to be defined by their well-known meanings in the art.

Foamable Pharmaceutical Compositions

The present subject matter provides simple and elegant foamable suspension gels that surprisingly maintain the chemical and physical stability of at least one active agent in a suspension that forms a homogenous foam. The foamable suspension gels are aqueous and optionally, alcohol-free and/or oil-free. The present suspension gels are foamable, break down with mechanical shear, but are not so-called alcoholic "quick-break" foams.

Moreover, the gel formulation in the can or container can be a post-foaming gel, which foams once released from the can. This innovative formulation provides extended shelf-life coupled with ease of application. For example, benzoyl peroxide is known to degrade clindamycin. However, the current foamable suspension gel formulation advantageously provides for both stability and ease of application.

In some embodiments, the foamable suspension gel is oil-free. In this regard, the phrase "oil-free" as used herein refers to compositions containing less than 1% by weight oil. In some embodiments, the foamable suspension gel is alcohol-free. In this regard, the phrase "alcohol-free" as used herein refers to compositions containing less than 1% by weight alcohol. Alcohol in this regard includes ethanol, isopropanol, n-propanol, butanol, or any other short chain aliphatic alcohol. In some embodiments, the foamable suspension gel is oil-free and alcohol-free.

a. Components

Components of the present foamable suspension gels can comprise or consist of a first active agent sparingly soluble to insoluble in water, an aqueous phase, a thickening agent, and water. The foamable suspension gels can comprise a second active agent. Optionally, the foamable suspension gels include one or more of a pH-adjusting agent (e.g., an acid, a base, a buffering agent, a buffering pair), a wetting agent/dispersing agent, a surfactant, a sun filter, a third active agent, an antioxidant, an additional foaming agent, a chelating sequestering agent, or a propellant. The foamable suspension gels can be alcohol-free and/or oil-free.

i. Active Agents

1. First Active Agent

The first active agent in the foamable suspension gel is sparingly soluble to insoluble in water, and is dispersed or suspended in the aqueous phase. Exemplified categories of active agents that are sparingly soluble to insoluble in water include, for example, analgesics, anesthetics, anti-inflammatory agents, antipyretics, antimicrobial agents such as, for example, antibacterial agents, antibiotics, and antifungals, antidepressants (e.g., nortriptyline hydrochloride), antiepileptics (e.g., methsuximide, phenobarbital, primidone), antimalerial agents (e.g., quinine sulfate), antimigraine agents (e.g., dihydroergotamine mesylate, ergotamine tartrate, methysergide maleate), antineoplastic agents (e.g., testolactone), immunosuppressants, antiprotozoal agents (e.g., metronidazole), antianxiolytic agents, antipsychotics, antihistamines, cardiovascular agents, corticosteroids, sex hormones, cough suppressants (e.g., dextromethorphan hydrobromide, guaifenesin, terpin hydrate), dermatological agents, diagnostic agents (e.g., indigotindisulfonate sodium), disinfectants, dopaminergic agents (e.g., apomorphine hydrochloride), antimuscarinic agents (e.g., atropine, isopropamide iodide, procyclidine hydrochloride), parasympathomimetics (e.g., physostigmine salicylate), sympathomimetics (e.g., xylometazoline hydrochloride, isoxsuprine hydrochloride), thyroid and antithyroid agents (e.g., iodine, levothyroxine sodium), skeletal muscle relaxants (e.g., carisoprodol, methocarbamol), stimulants and anorexiants (e.g., doxapram hydrochloride), gastrointestinal agents, immunomodulators, peptides, vitamins and vitamin derivatives, azoles, oxides and xanthines (e.g., caffeine), salts or derivatives thereof, and mixtures thereof In some preferred embodiments, the first active agent is selected from the group consisting of an antibacterial, an antibiotic, an antifungal, an immunomodulator, a peptide, a vitamin, a vitamin derivative, an azole, an oxide, salts or derivatives thereof, and mixtures thereof. In some embodiments, the first active agent is selected from the group consisting of benzoyl peroxide, a retinoid, a steroid, an azole antimicrobial agent, precipitated sulfur, and mixtures thereof Suitable concentration ranges of the first pharmaceutically active compound can be, for example, up to about 40% w/w, for example, in the range of about 0.5-40%, 1-20%, 2-10% w/w, or about 0.5%, 0.8%, 1%, 1.5%, 2%, 2.5%, 3%, 5%, 7.5%, 10%, 15%, 20%, 25%, 30%, 35%, or 40% w/w.

In some embodiments, the first active agent is benzoyl peroxide (BPO), that can be present in an amount from about 1% to about 25%, from about 1% to about 8%, from about 2% to about 8%, from about 4% to about 8%, from about 4% to about 10% for example, about 1%, 1.5%, 2%, 2.5%, 3%, 4%, 5%, 6%, 7%, 7.5%, 8%, 8.5%, 9%, 9.5%, 10%, 15%, 20%, or 25%.

Exemplified analgesics, anti-inflammatory agents and antipyretics include, for example, aminohippuric acid, anileridine, aspirin, codeine, codeine sulfate, indomethacin, levorphanol tartrate, pentazocine, pentazocine hydrochloride, propoxyphene napsylate, salts or derivatives thereof, and mixtures thereof Exemplified anesthetics include, for example, benzocaine, butamben, cocaine, dibucaine, dyclonine hydrochloride, tetracaine, salts or derivatives thereof, and mixtures thereof Exemplified antibacterial agents include, for example, chloramphenicol, chlortetracycline hydrochloride, clioquinol, demeclocycline, demeclocycline hydrochloride, erythromycin, methacycline hydrochloride, nalidixic acid, nitrofurazone, oxytetracycline, oxytetracycline calcium, penicillins (e.g., penicillin G, penicillin G benzathine, penicillin G sodium, and penicillin V benzathine), pyrazinamide, sulfadiazine, sulfamethizole, sulfamethoxazole, sulfapyridine, sulfisoxazole, tetracycline, salts or derivatives thereof, and mixtures thereof Exemplified antihistamines include, for example, cyclizine hydrochloride, cyproheptadine hydrochloride, hydroxyzine pamoate, phenindamine tartrate, thiethylperazine maleate, salts or derivatives thereof, and mixtures thereof Exemplified anti-anxiolytics include, for example, chlordiazepoxide, diazepam, droperidol, haloperidol, oxazepam, pentobarbital, pimozide, thiothixene, triazolam, salts or derivatives thereof, and mixtures thereof Exemplified cardiovascular agents include, for example, acenocoumarol, acetyldigitoxin, apraclonidine hydrochloride, enalaprilat, hydroflumethiazide, methyclothiazide, nifedipine, quinidine sulfate, trichlormethiazide, salts or derivatives thereof, and mixtures thereof Exemplified corticosteroids include, for example, betamethasone, betamethasone acetate, betamethasone valerate, clobetasol propionate, desonide, flumethasone pivalate, fluocinolone acetonide, fluorometholone, methylprednisolone, methylprednisolone acetate, prednisolone, prednisolone acetate, prednisolone hemisuccinate, prednisone, salts or derivatives thereof, and mixtures thereof Exemplified dermatological agents include, for example, abrasive agents, acitretin, adapalene, benzoyl peroxide, calamine, calcipotriene, dithranol, etretinate, fumaric acid, isotretinoin, metal oxides, pumice, pyrithione zinc, salicylic acid, selenium sulfide, precipitated sulfur, tacalcitol, talc, tars, titanium dioxide, tretinoin, zinc oxide, salts or derivatives thereof, and mixtures thereof Exemplified disinfectants include, for example, ascorbyl palmitate, benzoic acid, chlorobutanol, chlorocresol, chloroxylenol, halazone, methylparaben, nitromersol, phenylmercuric acetate, phenylmercuric nitrate, propylparaben, sorbic acid, thymol, salts or derivatives thereof, and mixtures thereof Exemplified vitamins and nutritional agents include, for example, vitamin A, vitamin E, vitamin K, cyanocobalamin, hydroxocobalamin, niacin, saccharin, thiamine mononitrate, salts or derivatives thereof, and mixtures thereof Exemplified sex hormones include, for example, dydrogesterone, estradiol cypionate, estropipate, norethindrone acetate, oxandrolone, oxymetholone, stanozolol, salts or derivatives thereof, and mixtures thereof Exemplified gastrointestinal agents include, for example, bisacodyl, docusate calcium, docusate sodium, magnesium hydroxide, sennosides, sulfasalazine, salts or derivatives thereof, and mixtures thereof Other active agents of interest that are sparingly soluble to insoluble in water include, for example, betadex, calcium hydroxide, calcium sulfate, camphor, disulfuram, ethyl vanillin, methylergonovine maleate, papaverine hydrochloride, sucrose octaacetate, vanillin, salts or derivatives thereof, and mixtures thereof Further examples of sparingly soluble to insoluble active agents can be found, for example, in *Martindale: The Complete Drug Reference*, Sweetman, 2004, Pharmaceutical Press, and in Martindale, *Martindale: The Extra Pharmacopoeia,* 31st Edition, 1996, Amer. Pharmaceutical Assn., which is herein incorporated by reference.

In one embodiment, the first active agent is benzoyl peroxide. Benzoyl Peroxide (CAS No. 94-36-0) can be commercially purchased from, for example, Sigma-Aldrich Chemicals, St. Louis, Mo.

In one embodiment, the first active agent is one or more azole antimicrobial or antifungal agents, for example, one or more of an imidazole or a triazole, including nitrate forms. The imidazole can be, for example, clotrimazole, miconazole, metronidazole, ketoconazole, econazole, butoconazole, oxiconazole, sulconazole, or mixtures thereof. The triazole can be, for example, albaconazole, ravuconazole, voriconazole, posaconazole, terconazole, itraconazole, and fluconazole. In one embodiment, the azole antimicrobial is metronidazole. In one embodiment, the azole antimicrobial is ketoconazole. Further information regarding azole antimicrobials can be found, for example, in *Goodman and Gilman's The Pharmacological Basis of Therapeutics*, Goodman, et al., eds., 11th Edition, 2005, McGraw-Hill. Additional antimicrobial agents and/or antifungal agents are further contemplated as useful herein, including by way of non-limiting example ciclopirox, ciclopirox olamine, terbinafine, tea tree oil, griseofulvin, undecylenic acid, salicylic acid, tolnaftate, amphotericin, candicidin, flucytosine, natamycin, nystatin, undecenoic acid, salts or derivatives thereof, and mixtures thereof In one embodiment, the first active agent is one or more retinoids, for example, vitamin A, retinol (cis or trans), retinal (cis or trans), retinoic acid (cis), tretinoin, hydroxyretretinol, didehydroretinoic acid, etretinate, retinyl palmitate, β-carotene, tazarotene, acitretin, adapalene, salts or derivatives thereof, and mixtures thereof. Further information regarding retinoids can be found, for example, in *Goodman and Gilman's The Pharmacological Basis of Therapeutics, supra.*

2. Second Active Agent

The second active agent can be any pharmaceutically active agent suitable for topical administration. The second active agent can be soluble in water, or sparingly soluble to insoluble in water. The second active agent can effect a pharmaceutical response that complements the first active agent, or that is independent of the first active agent, as desired. The second active agent can be, for example, antimicrobial agents such as antibacterials, antibiotics, and antifungals, immunomodulators, peptides, vitamins and vitamin derivatives, azoles, oxides, salts or derivatives thereof, and mixtures thereof. In one embodiment, the second active agent is an anti-acne agent.

In one embodiment, the second active agent is selected from the group consisting of a lincomycin antibiotic (e.g., clindamyin, lincomycin), a retinoid, sodium sulfacetamide, or salicylic acid.

Suitable concentration ranges of the second pharmaceutically active compound can be, for example, up to about 2%, 5%, 7%, 10%, 12%, 15%, 20%, 25%, 30%, 35%, or 40% w/w, for example, in the range of about 0.01-10%, 0.1-8%, 0.2-5%, 0.5-2%, or 5-40% w/w, or about 0.1%, 0.2%, 0.5%, 0.8%, 1%, 1.5%, 2%, 2.5%, 3%, 5%, 6%, 7%, 7.5%, 8%, 8.5%, 9%, 9.5%, 10%, 12%, 15%, 20%, 25%, 30%, 35%, or 40% w/w.

In one embodiment, the second active agent is clindamycin, a pharmaceutically acceptable salt or prodrug thereof. Clindamycin is an antibiotic also known as methyl 7-chloro-6,7,8-trideoxy-6-(1-methyl-trans-4-propyl-L-2-pyrrolidinecarboxamido)-1-thio-L-threo-α-D-galacto-octo-pyranoside or methyl 7-chloro-6,7,8-trideoxy-6-[[(1-methyl-4-propyl-2-pyrrolidinyl)carbonyl]amino]-1-thio-L-threo-α-D-galacto-octo-pyranoside. As used herein, the term "clindamycin" alone includes free-base clindamycin as well as the pharmaceutically acceptable salts and esters thereof. Examples of pharmaceutically acceptable salts and esters of clindamycin include, but are not limited to, clindamycin hydrochloride, clindamycin phosphate, clindamycin palmitate, and clindamycin palmitate hydrochloride. A clindamycin salt or ester can be used in the present compositions, for example, clindamycin phosphate.

The uses, properties, and methods of synthesis of clindamycin are set forth in U.S. Pat. No. 3,969,516, Stoughton, issued Jul. 13, 1976; U.S. Pat. No. 3,475,407, Bierkenmeyer, issued in 1969; U.S. Pat. No. 3,487,068, issued in 1969; U.S. Pat. Nos. 3,509,127 and 3,544,551, Kagan and Magerlein, issued in 1970; U.S. Pat. No. 3,513,155, Bierkenmeyer and Kagan, issued in 1970; Morozowich and Sinkula, U.S. Pat. No. 3,580,904, issued in 1971 and U.S. Pat. No. 3,655,885, issued in 1972; U.S. Pat. No. 3,714,141, issued in 1973; U.S. Pat. No. 4,568,741, issued in 1986; and U.S. Pat. No. 4,710, 565, issued in 1984. All of the foregoing patents are hereby incorporated herein by reference.

Additional knowledge in the art concerning clindamycin is found in, for example, Magerlein, et al., *Antimicro. Ag. Chemother.* 727 (1966); Birkenmeyer and Kagan, *J. Med. Chem.,* 13, 616 (1970); Oesterling, *J. Pharm Sci.* 59, 63 (1970); McGehee, et al., *Am. J. Med. Sci.* 256, 279 (1968); D. A. Leigh, *J. Antimicrob. Chemother.* 7 (Supplement A), 3 (1981); J E Gray et al., *Toxicol. Appl. Pharmacol.* 21, 516 (1972), and L W Brown and W F Beyer in *Analytical Profiles of Drug Substances*, Vol. 10, K. Florey, editor (Academic Press, New York, 1981), pages 75-91.

Clindamycin phosphate and clindamycin hydrochloride are commercially available from, for example, Sigma-Aldrich, St. Louis, Mo. and Abbott Laboratories, Chicago, Ill.

In one embodiment, the second active agent is one or more retinoids, for example, vitamin A, retinol (cis or trans), retinal (cis or trans), retinoic acid (cis), tretinoin, hydroxyretroretinol, didehydroretinoic acid, etretinate, retinyl palmitate, β-carotene, tazarotene, acitretin, adapalene, salts or derivatives thereof, and mixtures thereof In one embodiment, the second active agent is sodium sulfacetamide.

In some embodiments, the first active agent and the second active agent are the same, but the first active agent is suspended and the second active agent is dissolved or solubilized. In this manner, the suspended first active agent has a different rate of release than the solubilized second active agent. By tailoring the rate of release, it is possible to advantageously effect the rate of penetration of the active ingredient. For example, in certain embodiments, the solubilized active agent penetrates faster into the epidermis whereas the suspended active agent exhibits slow release and therefore slower penetration. Those of skill in the art will know of other ways to tailor the active agents in order to manifest beneficial rates of penetration.

In some embodiments, the second active agent is selected from the group consisting of an antibacterial, an antibiotic, an antifungal, an immunomodulator, a peptide, a vitamin, a vitamin derivative, an azole, an oxide, salts or derivatives thereof, and mixtures thereof. In some embodiments, the second active agent is selected from the group consisting of a lincomycin antibiotic, a retinoid, sodium sulfacetamide, salicylic acid, salts or derivatives thereof, and mixtures thereof. In some embodiments, the second active agent is a lincomycin antibiotic, for example, lincomycin or clindamycin, salts or derivatives thereof, or mixtures thereof, or a macrolide antibiotic, by way of non-limiting example, clarithromycin, azithromycin, erythromycin, salts or derivatives thereof, or mixtures thereof. In one embodiment, the second active agent is clindamycin phosphate, which can be present in an amount from about 0.2% to about 2.5%, for example, about 0.2%, 0.5%, 0.8%, 1%, 1.5%, 2%, or 2.5%.

As desired, the second active agent can be soluble or sparingly soluble to insoluble in water. The second active agent can be dissolved, solubilized or in a suspension.

In some embodiments, the first active agent or the second active agent is a retinoid. In some embodiments, the retinoid is selected from the group consisting of vitamin A, retinol (cis or trans), retinal (cis or trans), retinoic acid (cis), tretinoin, hydroxyretroretinol, didehydroretinoic acid, etretinate, retinyl palmitate, β-carotene, tazarotene, acitretin, adapalene, salts or derivatives thereof, and mixtures thereof In one embodiment, the first active agent is benzoyl peroxide and the second active agent is clindamycin phosphate. In another embodiment, the first active agent is tretinoin and the second active agent is clindamycin phosphate. In a further embodiment, the first active agent is metronidazole and the second active agent is sodium sulfacetamide. In another embodiment, the first active agent is benzoyl peroxide and the second active agent is tretinoin.

In some embodiments, wherein if the second active agent comprises an antibiotic, the second active agent preferably comprises an additional active agent. In some embodiments the second active agent comprises or consists of one or more antibiotics and an additional active agent.

3. Third Active Agent

In some embodiments, the foamable suspension gels further comprise a third active agent. The third active agent can be any pharmaceutically active agent suitable for topical administration. The third active agent can be soluble in water, or sparingly soluble to insoluble in water.

In some embodiments, the third active agent can be, for example, antibacterials, antibiotics, antifungals, immunomodulators, peptides, vitamins and vitamin derivatives, azoles, oxides, salts or derivatives thereof, and mixtures thereof. In some embodiments, the third active agent is a topically applied anti-acne agent different from either the first or second active agents. Any topical anti-acne agent known in the art can be included as a third active agent in the foamable suspension gels. Exemplified anti-acne agents include retinoids, antibiotics, azole antimicrobials, vitamins, and the like.

In some embodiments, the anti-acne agent is an antibiotic, an antimicrobial azole, a retinoid, or a vitamin (e.g., a vitamin A, a vitamin B, a vitamin C, a vitamin E). As desired, the third active agent can be soluble or sparingly soluble to insoluble in water. The third active agent can be dissolved, solubilized or suspended in the gel.

In some embodiments, the third active agent is a sun filter, as described below.

ii. Dispersing Agents/Wetting Agents

Active agents that are sparingly soluble to insoluble in water (i.e., are hydrophobic), can require a dispersing agent or wetting agent to coat the surface of the hydrophobic particles, thereby lowering their surface tension. The dispersing agent and the wetting agent can be the same agent or two or more different agents. A dispersing/wetting agent can help to maintain the hydrophobic particles in the formulation matrix and aiding in the distribution of the hydrophobic active agent upon the skin. U.S. Pat. No. 5,470,884 discusses the benefits of a dispersing/wetting agent with reference to formulations containing benzoyl peroxide.

In some embodiments, the aqueous phase can comprise a dispersing/wetting agent. The dispersing/wetting agent can be provided to facilitate the suspension of the first active agent in the aqueous phase. In some embodiments, the dispersing/wetting agent is a surfactant.

In the foamable suspension gels of the present subject matter, active agents sparingly soluble to insoluble in water are suspended in the aqueous phase. Suspension can be facilitated by inclusion of a dispersing/wetting agent in the aqueous phase. The dispersing/wetting agent allows the sparingly soluble to insoluble active agent to be dispersed or wetted with water.

The dispersing/wetting agents can have surfactant properties. Suitable dispersing/wetting agents break up the majority of the hydrophobic particles of the active agent sparingly soluble to insoluble in water into primary particle form and allow for easy redispersion of settled particles.

In some embodiments, the dispersing/wetting agent is a non-ionic surfactant. Exemplified dispersing/wetting agents for use in the present foamable suspension gels include sodium dioctyl sulfosuccinate, Brij®-30 (Laureth-4), Brij®-58 (Ceteth-20) and Brij®-78 (Steareth-20), Brij®-721 (Steareth-21), Crillet-1 (Polysorbate 20), Crillet-2 (Polysorbate 40), Crillet-3 (Polysorbate 60), Crillet 45 (Polysorbate 80), Myrj-52 (PEG-40 Stearate), Myrj-53 (PEG-50 Stearate), Pluronic® F77 (Poloxamer 217), Pluronic® F87 (Poloxamer 237), Pluronic® F98 (Poloxamer 288), Pluronic® L62 (Poloxamer 182), Pluronic® L64 (Poloxamer 184), Pluronic® F68 (Poloxamer 188), Pluronic® L81 (Poloxamer 231), Pluronic® L92 (Poloxamer 282), Pluronic® L101 (Poloxamer 331), Pluronic® P103 (Poloxamer 333), Pluracare® F 108 NF (Poloxamer 338), and Pluracare® F 127 NF (Poloxamer 407). In some embodiments, the dispersing/wetting agent is Pluronic® F68 (Poloxamer 188). In one embodiment, the dispersing/wetting agent is a Pluronic® (Poloxamer). In one embodiment, the dispersing/wetting agent is Pluronic® F68 (Poloxamer 188). Pluronic® polymers are commercially purchasable from BASF, USA and Germany.

A wide variety of other surfactants can also be employed in the present foam compositions, if desired. These surfactants can include, for example, polyoxyethylene fatty ethers, polyoxyethylene fatty esters, fatty acids, sulfated fatty acids, phosphated fatty acids, sulfosuccinates, amphoteric surfactants, non-ionic poloxamers, non-ionic meroxapols, petroleum derivatives, aliphatic amines, polysiloxane derivatives, sorbitan fatty acid esters, pharmaceutically acceptable salts thereof, and mixtures thereof. In particularly preferred embodiments in this regard, the surfactant can be selected from the group consisting of laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and mixtures thereof Other surfactants commonly known as useful in the preparation of foamable compositions are further contemplated as within the scope of the present subject matter. These other surfactants include, for example, those listed in the *CTFA Cosmetic Ingredient Dictionary*, Second Edition, The Cosmetic Toiletry and Fragrance Association, Inc., 1133 Fifteenth Street, N.W., Washington, D.C. 20005, 1977, the entire contents of which are hereby incorporated by reference.

The foamable suspension gels generally contain up to about 1%, 2%, 3%, 4%, 5% (w/w) dispersing/wetting agent, for example in the range of 0.2-5%, 0.5-3%. In some embodiments, the foamable suspension gels contain about 0.2%, 0.5%, 0.8%, 1%, 1.5%, 2%, 2.5%, 3%, 4%, or 5% dispersing/wetting agent.

In some embodiments, the dispersing/wetting agents possess surfactant properties, and the foaming suspension gels do not require an additional surfactant. Generally, inclusion of a surfactant is optional.

In some embodiments, the thickening agent can be used as a dispersing agent in addition to a thickening agent. In such formulations, the foaming suspension gels do not require a distinct dispersing/wetting agent or an additional surfactant. Addition of a distinct dispersing/wetting agent or an additional surfactant is optional.

A dispersing and/or wetting agent is not generally considered to be a foaming agent. In fact, foaming can be a disfavored attribute for these types of surfactants. Efficient wetting of a surface occurs when the cohesive forces between hydrophobic regions of adsorbed surfactant molecules are minimized Cohesion between hydrophobic regions is minimized by increasing the size of the hydrophilic region(s) relative to the hydrophobic region(s) for a given wetting agent. Similarly, decreasing the size of the hydrophobic region(s) relative to the hydrophilic region(s) minimizes the cohesion between hydrophobic regions. For good foaming to occur, the cohesive forces between adsorbed surfactant molecules must be greater than the cohesive forces required for good wetting. Therefore a good wetting agent is typically considered a poor foaming agent and vice versa. See, page 218 of Schönfeldt, *Surface Active Ethylene Oxide Adducts,* 1969, Pergamon Press.

iii. Thickening Agents

The foamable suspension gels contain one or more thickening or suspension agents that provide a suitable viscosity and are in an amount that is sufficient to hold the active agent which is sparingly soluble to insoluble in water in a suspension. The thickening agent can be substantially chemically inert. The thickening agent can be synthetic or naturally occurring.

The amount of thickening agent is sufficient to maintain the active agent which is sparingly soluble to insoluble in water in suspension, while maintaining a pourable gel that can be efficiently and evenly released from a container. The foamable suspension gels can contain up to about 5% thickening agent, usually up to about 3% or 2% thickening agent. In some embodiments, the foamable suspension gels contain in the range of about 0.1-2%, 0.8-1.5% thickening agent, for example, about 0.1, 0.2, 0.5, 0.8, 1, 1.3, 1.5, 2% thickening agent. In some embodiments, the amount of thickening agent included will result in a foamable gel having a viscosity of less than about 40,000 centipoises (cP), for example, in the range of about 1,000 to about 20,000 cP.

The thickening agent can be substantially chemically inert to other ingredients. The thickening agent can be synthetic or naturally occurring. In some embodiments, the thickening agent is a hydrocolloid, for example, selected from the group consisting of agar, alginate, arabinoxylan, carrageenan, carboxymethylcellulose, hydroxypropyl methylcellulose, cellulose, curdlan, gelatin, gellan, β-glucan, guar gum, gum arabic, locust bean gum, pectin, starch, a carbomer, acrylate copolymers, silica, xanthan gum, salts or derivatives thereof, and mixtures thereof. In some embodiments, the thickening agent is a natural gum, for example, selected from the group consisting of gum arabic, tragacanth gum, xanthan gum, carrageenan (alginate gum), pectin, guar gum, salts or derivatives thereof, and mixtures thereof.

In some embodiments, the thickening agent is xanthan gum or a carbomer. In some embodiments, the thickening agent is xanthan gum. In some embodiments, the thickening agent can be selected from the group consisting of a hydrocolloid, a natural gum, and mixtures thereof.

In some embodiments, the thickening agent is xanthan gum. The xanthan gum can be food grade or a pharmaceutical grade (USP/NF). Exemplified xanthan gums suitable for use in the present foamable suspension gels include Keltrol F, Xantural 11K, Xantural 75, Xantural 180. Food grade and pharmaceutical/cosmetic grade xanthan gum formulations are commercially available from, for example, CP Kelco, Atlanta, Ga.

iv. Water

The present foamable suspension gels are aqueous.

The foamable suspension gels contain at least about 20%, 30%, 40%, 50%, 60%, 65%, 70%, 75%, 80%, 85%, 86%, 87%, 88%, 89%, 90%, 91%, 92%, 93%, 94%, 95%, 96%, 97%, 98%, 99% water. In some embodiments, the foamable suspension gels contain in the range of about 86-95%, 87-94%, 87-95%, 88-93%, or 89-92% water. In some embodiments, the foamable suspension gel comprises at least about 30% water.

Water content can be measured using techniques well known in the art, including for example, using a coulometer (Metrohm K F, Herisau, Switzerland).

v. pH-Adjusting Agents

The foamable suspension gels can comprise a pH-adjusting agent, for example, an acid, a base, a buffering pair, or a buffering agent. In some embodiments, the pH-adjusting agent is a buffering agent, for example, a buffering pair to stably maintain a desired pH. The chosen buffering agent or buffering pair selected will depend on the active ingredients included in the gel. An appropriate buffer may have a pKa value that is at or near the desired pH.

In some embodiments, the desired pH is an acidic pH. Exemplified buffering agents to maintain an acidic pH include, for example, citric acid/citrate, acetic acid/acetate, BICINE, HEPES, Trizma. In some embodiments, the desired pH is a neutral pH. Exemplified buffering agents to maintain a neutral pH include HEPES, TRIS, phosphoric acid/phosphate, Trizma. In some embodiments, the desired pH is a basic pH. Exemplified buffering agents to maintain a basic pH include TRIS, Trizma, HEPES, carbonate/bicarbonate. These and additional biological buffers are available from Sigma-Aldrich, St. Louis, Mo. or Merck, Darmstadt, Germany. The buffering agent can also be an amino acid, for example, glycine, histidine, arginine, lysine, asparagine, aspartic acid, glutamine, glutamic acid. In certain instances, it may be appropriate to add an acid or a base, for example, HCl, NaOH, KOH to arrive at the proper pH value.

In formulations including benzoyl peroxide and clindamycin, the buffering pair can be citric acid and citrate.

The buffering agent or buffering pair can be included at a concentration of up to about 1%, usually up to about 0.3%, 0.5%, 0.7%, or in a range of about 0.1-1.0%, 0.3-0.8%. The foamable suspension gels can contain about 0.1%, 0.2%, 0.3%, 0.4%, 0.5%, 0.6%, 0.8%, 0.9%, or 1.0% (w/w) of a buffering agent or a buffering pair.

In some embodiments, the pH-adjusting agent is a buffering agent or a buffering pair, for example, an amino acid, a citrate buffer, a phosphate buffer, a bicarbonate buffer, a TRIS buffer, or a HEPES buffer. In some embodiments, the foamable suspension gel has a pH between about 3-9, about 4-9, about 4-6, or about 4-5.5. In some embodiments, the foamable suspension gel has a pH of about 4, 4.1, 4.2, 4.3, 4.4, 4.5, 4.6, 4.7, 4.8, 4.9, 5, 5.1, 5.2, 5.3, 5.4 or 5.5.

vi. Antioxidants

In some embodiments, the foamable suspension gels can comprise one or more antioxidants or free radical scavengers to maintain the desired physical and chemical properties. Suitable antioxidants do not themselves initiate the decomposition of an active agent, and are soluble in the present formulations. Exemplified antioxidants include oxygen, quinones, co-enzyme Q, polymerizable monomers, butylated hydroxyanisole (BHA), butylated hydroxytoluene (BHT), ascorbic acid, ascorbyl palmitate, t-butyl hydroquinone, disodium ethylenediamine tetraacetic acid (EDTA), erythorbic acid, olive (olea eurpaea) oil, pentasodium penetetate, pentetic acid, propyl gallate, sodium ascorbate, sodium metabisulfite, sodium sulfite, tocopheryl, and tocopheryl acetate.

An antioxidant can be included at a concentration up to about 0.5%, more usually up to about 0.1% or 0.2% (w/w), for example, about 0.1%, 0.15%, 0.2%, 0.25%, 0.3%, 0.4%, or 0.5%.

Inclusion of an antioxidant is optional. In some embodiments, the foamable suspension gels are free of an antioxidant.

vii. Chelating/Sequestering Agents

Chelating and sequestering agents can aid in delaying the initiation of free radical formation with divalent trace metal cations. Including a chelating agent into the formulation can be advantageous in formulations that are packaged in a metal container. An exemplified chelating/sequestering agent is ethylenediamine tetraacetic acid (EDTA).

A chelating/sequestering agent can be included at a concentration up to about 0.5%, more usually up to about 0.1% or 0.2% (w/w), for example, about 0.1%, 0.15%, 0.2%, 0.25%, 0.3%, 0.4%, or 0.5%.

viii. Sun Filters

In some embodiments the foamable suspension gels of the present subject matter further comprise one or more sun filters, sunscreen, sunblock, or any other sun-blocking components or agents. Any sun filters known in the art are suitable in the present compositions, including UVA and/or UVB sun filters.

Exemplified sun filters include Aminobenzoic acid (4-Aminobenzoic acid); Avobenzone (4-tert-butyl-4-methoxydibenzoylmethane); Benzophenone-2 (Bis(2,4-Dihydroxyphenyl)Methanone); Benzophenone-3 (Oxybenzone); Benzophenone-4 (Sulisobenzone); Benzophenone-5 (Sulisobenzone sodium); Benzophenone-8 (Dioxybenzone); Benzylidene Camphor (3-(4-Methylbenzylidene)-d-1 camphor); Cinoxate; Ecamsule (Terephthalylidene dicamphor sulfonic acid); Ethoxylated ethyl 4-aminobenzoic acid (PEG25 PABA, e.g., Uvinul® P25); Homosalate (Homomethyl salicylate); Isoamylmethoxycinnamate (Isopentenyl-4-methoxycinnamate); Isopropylbenzyl salicylate; Menthyl anthranilate (Methyl 2-aminobenzoate); Mexoryl XL (phenol, 2-(2H-benzotriazol-2-yl)-4-methyl-6[2-methyl-3-[1,3,3,3-tetramethyl-1-[(trimethylsilyl)oxy]disiloxanyl]propyl) Octyl dimethyl PABA; Octinoxate (Octyl methoxycinnamate); Octyl salicylate (2-Ethylhexyl Salicylate); Octocrylene (2-cyano-3,3-diphenyl acrylic acid, 2-ethyl hexyl ester); Octyl triazone (2,4,6-Trianalino-(p-Carbo-2'-ethylhexyl-1'oxy) 1,3,5-Triazine); Padimate O (2-Ethylhexyl 4-dimethylaminobenzoate); Phenylbenzimidazole sulfonic acid (2-Phenylbenzimidazole-5-sulfonic acid) and its potassium, sodium and triethanolamine salts; N,N,N-Trimethyl-4-(oxoborn-3-ylidenemethyl) anilinium methylsulfate; Salicylic acid salts (potassium, sodium and triethanolamine); Tinosorb® M (2,2'-Methylene-bis-6-(2H-benzotriazol-2-yl)-4-(tetramethyl-butyl)-1,1,3,3-phenol); Titanium dioxide; Triethanolamine salicylate; Zinc oxide; salts or derivatives thereof; and mixtures thereof. Additional suitable sunscreen components are described, for example, in International Publication No. WO 2004/071479, and in co-owned, co-pending U.S. patent application Ser. No. 11/187,217, the disclosures of which are hereby incorporated herein by reference in their entirety for all purposes.

The compositions generally can contain about 1% to about 25% total (w/w) of one or more sun filters. In some embodiments, the foamable suspension gels will contain about 2%-10%, 4%-8%, 2%-6%, or about 1%, 2%, 3%, 4%, 5%, 6%, 7%, 8%, 9%, 10%, 11%, 12%, 13%, 13%, 14%, 15%, 20%, or 25% w/w total of one or more sun screen components.

In some embodiments, the sun filter is a water dispersable, inert sun filter, for example, titanium dioxide.

ix. Solvents

In certain optional embodiments, the foamable suspension gels of the present subject matter further comprise a volatile solvent, for example, an alcohol. Suitable alcohols include lower alkanols ($C_1$-$C_6$ alcohols). Alkanols can be butanol, isobutanol, propanol, isopropanol, ethanol, methanol and mixtures thereof. In certain embodiments, the alkanol is ethanol. In one embodiment, the volatile solvent (e.g., alcohol) is present in an amount up to 5% w/w, for example, 1%, 2%, 3%, 4%, or 5% of the total composition. In certain embodiments, a volatile solvent or alcohol is optional, so that the formulation is non-alcoholic.

x. Propellants

The present foamable suspension gels can contain a propellant. Depending on the relative densities of the foamable suspension gel base and the propellant, the propellant can be dispersed within the gel, dissolved within the gel, or layered over or under the gel. Exemplified aerosol propellants of use include, for example, hydrocarbons, chlorofluorocarbons, dimethyl ether, hydrofluorocarbons, compressed gases, or mixtures thereof.

The maximum amount of propellant used can be determined by its miscibility with other components in the composition to form a mixture, such as a homogeneous mixture. The minimal level of propellant used in the composition can be determined by the desired foam characteristics, and its ability to substantially or completely evacuate the container.

The propellant concentration can be up to about 20%, usually up to about 5% or 10%, for example, in the range of about 2-15%, 3-10%, 4-7% w/w relative to the total amount of composition, for example, about 2%, 3%, 4%, 5%, 6%, 7%, 8%, 9%, 10%, 11%, 12%, 13%, 14%, or 15% w/w. In one embodiment, the amount of propellant added to the foamable suspension gel compositions is about 2.8 g of propane/butane propellant for each about 50 g of the presently described foamable suspension gel bases.

In one embodiment, the propellant is a mixture of propane and butane. The present compositions can be packaged in a polyamide-imide-lined aluminum can and pressurized with a propane/butane mixture as the propellant. In one embodiment, the propellant can comprise or consist of a mixture of propane, n-butane, isobutene, and pentane. In one exemplified embodiment, the propellant can comprise or consist of about 55% propane, about 30% n-butane, and about 15% isobutane.

While chlorofluorocarbons (CFCs) can also be used as propellants, due to environmental concerns propellants can be hydrocarbons, in particular, propane, butane, pentane, or mixtures thereof. Other suitable propellants include dimethyl ether, nitrogen, argon, hydrofluorocarbons such as 134a and 227, and mixtures of any of the foregoing.

xi. Other Excipients

In some embodiments, the foamable suspension gel comprises preservatives, emollients, humectants, or other pharmaceutically acceptable excipients known in the art.

In addition to those enumerated above, any other dermatologically acceptable excipients commonly known to those of ordinary skill in the art as useful in topical compositions are contemplated as useful in the compositions described herein. Further, any non-toxic, inert, and effective topical carrier may be used to formulate the compositions described herein. Well-known carriers used to formulate other topical therapeutic compositions for administration to humans will be useful in these compositions. Examples of these components that are well known to those of skill in the art are described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful pharmaceutically acceptable excipients, carriers and diluents include distilled water, physiological saline, Ringer's solution, dextrose solution, Hank's solution, and DMSO, which are among those preferred for use herein.

These additional other inactive components, as well as effective formulations and administration procedures, are well known in the art and are described in standard textbooks, such as *Goodman and Gillman's: The Pharmacological Bases of Therapeutics,* 8th Ed., Gilman et al. Eds. Pergamon Press (1990) and *Remington's Pharmaceutical Sciences,* 17th Ed., Mack Publishing Co., Easton, Pa. (1990), both of which are incorporated by reference herein in their entirety.

b. Physicochemical Properties i. Viscosity

The foamable suspension gels have an appropriately balanced viscosity, that is sufficiently viscous to hold the one or more active agents in a suspension, but not so viscous so as to be unable to be expelled from a container. The suspension gels can have a viscosity that achieves a pourable gel and that allows the gel to be expelled easily and evenly from a container. A gel having a viscosity sufficient to maintain the one or more active agents in a suspension also aids in maintaining the chemical and physical stability of the active agents.

In some embodiments, the foamable suspension gels have a final viscosity of less than about 40,000 centipoises (cP), 20,000 cP, 15,000 cP, or 10,000 cP at 25° C. In some embodiments, the foamable suspension gel has a viscosity of about 5,000 cP, 6,000 cP, 7,000 cP, 8,000 cP, 9,000 cP, 10,000 cP, 12,000 cP, 15,000 cP, 18,000 cP, 20,000 cP, 25,000 cP, 30,000 cP, 35,000 cP, or 40,000 cP at 25° C. In some embodiments, the foamable suspension gel has a viscosity of about 1,000-20,000 cP, 5,000-15,000 cP, 6,000-12,000 cP, or 7,000-10,000 cP at 25° C. In some embodiments, the foamable suspension gel has a viscosity of about 5,000-15,000 at 25° C.

The viscosity of the foamable suspension gels can be measured with a suitable viscosity measuring device. Techniques include: (i) Brookfield Synchro-lectric rotating spindle viscometer, where the spindle is introduced into the suspension gel and viscosity is measured at a range of temperatures; and (ii) Brookfield Cone & Plate Viscometer, where samples of foam are introduced between the cone and plate and the rheology of the foam is determined over a range of shear rates and temperatures.

In a particularly preferred embodiment, the present foamable suspension gels have a viscosity permitting them to be delivered through an actuator.

ii. Density

The present foamable suspension gels have a density sufficient to maintain the active agents in a suspension. However, the density can be more or less than that of the active agents included in the suspension gel.

In some embodiments, the density at 25° C. of the foamable suspension gel concentrate is at least about 0.8 g/ml, in the range of about 0.8-1.5 g/ml, for example, about 0.8 g/ml, 0.9 g/ml, 0.95 g/ml, 1 g/ml, 1.05 g/ml, 1.1 g/ml, 1.15 g/ml, 1.2 g/ml, 1.25 g/ml, 1.3 g/ml, 1.35 g/ml, 1.4 g/ml, 1.45 g/ml, or 1.5 g/ml at 25° C.

In contrast, the foam density of the dispensed foam, after dispensing from the container, is preferable about 0.6 to about 0.9 g/ml at 25° C.

The density of the present foamable suspension gels can be measured with a suitable density determination apparatus. Techniques include: (i) pycnometer/weight per gallon cup, where the foamable suspension gel at fixed temperatures is carefully introduced into a fixed-volume vessel of known volume and mass; and (ii) Electronic density/specific gravity meter, where a slow stream of foamable suspension gel at fixed temperatures is introduced into a flow-through cell and the density is determined by the oscillating body method.

iii. pH

The pH of the foamable suspension gels will depend on the active agents included in the formulations. The final pH will promote the chemical and physical stability of the active agents.

In the embodiments where benzoyl peroxide and clindamycin are included in the foamable suspension gel, the pH is acidic, in the range of about 4.0-5.1 or 4.2-4.6 or 4.4-5.1, for example, about 4.00, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.00, 5.05, or 5.10.

pH values can be measured using techniques known in the art, for example, by using a pH meter and an appropriate probe.

iv. Particle Size of Active Agents

The particle size of the active agents included in the foamable suspension gels should be sufficiently small or fine to remain suspended in the gel and not settle out, to allow for a smooth feel upon administration of the foamable gel, and to release from the container without clogging the exit channel. The active agent particles should not be so small so as to become a tightly packed agglomeration that can not be redispersed upon shaking or so large that they settle out of the foamable suspension gel or impart a gritty feel to the foam. The particles can be of a uniform size or of varying sizes within a range of diameters. In one embodiment, greater than about 90% of the active agent particles are of a uniform size (i.e., monodispersed).

In some embodiments, the particle sizes of the active agents have an average diameter of in the range of about 0.5-100 μm, usually less than about 20 or 15 μm, more often an average diameter of less about 10 μm, usually in the range of about 5 μm to about 10 μm, for example, with an average diameter of about 5 μm, 6 μm, 7 μm, 8 μm, 9 μm, 10 μm, 20 μm, or 50 μm.

Particle size can be measured using techniques known in the art, including, for example, visual inspection using a microscope (e.g., 100× or 200× magnification).

The extent and rate of settling of particles can be monitored and quantified using techniques known in the art, for example, by subjecting aliquots to a Turbiscan analysis. Equipment for quantifying the turbidity or physical stability of a suspension gel can be purchased, for example, from Formulaction, l'Union (near Toulouse), France.

v. Pressure

The present foamable suspension gels can be packaged in a container. In some embodiments, the container is pressurized. The pressure in the container should be sufficient to allow the efficient expelling of the foamable gel. The pressure in the pressurized container should not be so high such that the gel releases without control as to application or amount. Also, lower pressures provide for the post-foaming of the gel upon release from the pressurized container.

In some embodiments of the present subject matter, the foamable suspension gel is in a single container. The container can be a pressurized container. In other embodiments, the foamable suspension gel may be in multiple containers.

In some embodiments, the gel is a post-foaming gel, which foams after release from a container, for example, a pump or pressurized container.

In some embodiments, the container is a non-pressurized container, for example, a pump, tube, bottle, jar, or any suitable dispensing package or device.

In some embodiments, the foamable suspension gel comprises an aerosol propellant. In some embodiments, the container is pressurized, and additionally contains a propellant. The pressure in the pressurized container is from about 5 psig to about 110 psig at 21-25° C., for example, about 5, 10, 15, 20, 25, 30, 35, 40, 45, 50, 55, 60, 65, 70, 75, 80, 85, 90, 100 or 110 psig at 21-25° C.

In some embodiments, the pressurized container is pressurized to about 63-80 psig, for example, about 63 psig, 64 psig, 65 psig, 66 psig, 67 psig, 68 psig, 69 psig, 70 psig, 71 psig, 72 psig, 73 psig, 74 psig, 75 psig, 76 psig, 78 psig, 79 psig, or 80 psig, as measured at 21-25° C.

vi. Stability

As used herein, stability refers to the chemical and physical integrity of the one or more active agents in the foamable suspension gels. One or more of the active agents may be subject to, for example, oxidation or chemical degradation.

Oxidation of an active agent can be monitored and quantified, for example, by using a color indicator that changes color in correlation to the presence or absence of oxidation or the extent of oxidation, for example, potassium iodide. The potassium iodide is colorless in the absence of oxidation, turns yellow in the presence of oxidation, and becomes brown with increasing oxidation. Color changes can be quantified using a spectrophotometer, for example, a Color Quest Color Measurement System, commercially available from Hunter Associates Laboratory, Reston, Va.

Chemical degradation of an active agent can be monitored and quantified, for example, using high performance liquid chromatography (HPLC). Methods for carrying out HPLC are well known in the art. See, for example, *High Performance Liquid Chromatography: Fundamental Principles and Practice*, Lough, et al., eds., 1996, Kluwer Academic Pub, and Meyer, *Practical High-performance Liquid Chromatography,* 2004, John Wiley & Sons. Degradation can be quantified by measuring the decrease of peak size (e.g., height of a peak or area under a peak) on the data output of peaks indicating undegraded active agent (e.g., benzoyl peroxide or clindamycin), and/or the increase of peak size of peaks indicating degraded active agent (e.g., benzoic acid or clindamycin sulfoxide isomers).

Stability can depend on time and temperature. Preferably, at least about 90%, 93%, 95%, or 97% of undegraded active agent is detected in the suspension gel formulation after at least about 3, 4, 5, 6 months at 5° C., 25° C. or 30° C. For example, the foamable suspension gels can retain at least about 80%, 85%, 90% undegraded active agent for at least 6 months at 25° C. The foamable suspension gels can retain at least about 90%, 95%, 96%, 97%, 98% undegraded active agent for at least 12 months, or at least 24 months at 5° C. The amount of undegraded active agent can be measured in comparison to the freshly prepared gel or in comparison to the amount of degraded active agent formed.

In some embodiments, the first and second active agents within the foamable suspension gel are chemically and physically stable for at least 3 months, 4 months, 5 months, 6 months at 5° C., 25° C. or 30° C. In some embodiments, the first and second active agents within the foamable suspension gel are chemically and physically stable for at least 12 months, or for at least 24 months, at 5° C.

Methods of Treating a Dermatological Condition

The present subject matter also provides for methods of therapeutically and prophylactically treating a dermatological condition by topically applying the foam of the foamable suspension gels of the present subject matter to affected areas. Exemplified dermatological conditions suitable for treatment by the present foamable suspension gels include rashes, eczema, contact dermatitis, acne (including acne vulgaris and acne rosacea), fungal infections, and bacterial infections. The foamable suspension gels are particularly suitable for treating acne.

Acne is treated both therapeutically and prophylactically by applying the foam of the foamable suspension gel to the skin in areas where acne lesions are present or likely to be present. The foam is generally rubbed into the skin until the foam is totally collapsed. The foam can be applied one, two, three, four or more times a day, as needed, or as directed by a healthcare provider. The collapsed foam may be left on the skin or washed off as desired depending upon the purpose of application. Alternatively, the foam may be applied as a facial mask and washed off after use.

Combination Therapy

In another preferred embodiment, the present preferred compositions may be used in combination with an additional pharmaceutical dosage form to enhance their effectiveness in treating a dermatological disease or disorder, particularly acne. In this regard, the present preferred compositions may be administered as part of a regimen additionally including any other pharmaceutical and/or pharmaceutical dosage form known in the art as effective for the treatment of a dermatological disorder. Similarly, a pharmaceutically active ingredient other than those specified herein can be added to the present preferred compositions to enhance their effectiveness in treating a dermatological disease or disorder. Accordingly, this additional pharmaceutically active ingredient or additional pharmaceutical dosage form can be applied to a patient either directly or indirectly, and concomitantly or sequentially, with the preferred compositions described herein.

In one embodiment in this regard, the present preferred composition and the additional pharmaceutical dosage form can be administered to a patient at the same time. In an alternative embodiment, one of the present preferred compositions and the additional pharmaceutical dosage form can be administered in the morning and the other can be administered in the evening.

Methods of Producing a Foamable Suspension Gel

The manufacturing process for the present foamable suspension gel base involves the preparation of several phases that are subsequently combined. This is largely due to the particulate nature of the first active agent that is sparingly soluble to insoluble in water.

In one approach, a "gel concentrate" is prepared by combining water and a thickening agent. Thereafter, the first active agent is mixed with a dispersing/wetting agent to form a homogenous dispersion while mixing. Mixing of the dispersion containing the first active agent is continued to prevent the first active agent from settling to the base of the mixing vessel and creating a solid "cake."

Next, the gel concentrate is admixed to the dispersion containing the first active agent during stirring to produce a physically stable gel holding the first active agent in suspension. The size of particles of the first active agent (and other active agents) in the gel can be reduced through a milling process.

Where the suspension gel is intended to include one or more second active agents, the following subsequent steps are undertaken. In a separate vessel, a gel containing a thickening agent and the second active agent is prepared. When the second active agent is a lincomycin antibiotic, such as clindamycin phosphate, no pH adjustment is necessary. That is, the pH of the solution containing clindamycin phosphate is below pH 5.5, below pH 5.2 or below pH 5, such as pH 4 to 4.5 (e.g., 4, 4.1, 4.2, 4.3, 4.4, or 4.5).

Subsequently, the gel containing the first active agent is blended with a gel containing the second active agent, resulting in a foamable suspension gel base containing the first and second active agents (and other active agents).

The foamable suspension gel base can then be added into the individual containers during the filling operation. The valves are fitted to the cans and crimped into place. In pressurized containers, a metered amount of propellant can be injected through the valve to complete the formulation. Another means of filling the cans involves a single-liquid-phase fill, in which the composition is kept warm to ensure homogeneity, followed by crimping and propellant injection. Yet another means involves formulating the entire composition, including the propellant, in bulk, under pressure, and then injecting the formulation into a crimped aerosol can.

The compositions made according to this method are preferably in an aerosol dosage form suitable for topical application. Accordingly, said production method can additionally comprise the further step of charging the container with a propellant suitable to effect aerosol delivery of the composition from the container.

The effectiveness of the present pharmaceutical formulations depends on achieving the proper combination of formulation, container, and valve assembly.

The Container

The instant foamable pharmaceutical compositions are preferably packaged in a container as an aerosol. The compositions may be packaged in the container using either a single-step or a multiple-step filling process commonly known to those of ordinary skill in the art.

The container must be selected to provide the aerosol formulation with a long shelf life. Accordingly, the container must be chemically inert with respect to the composition contained therein so as not to interfere with the stability of the formulation or with the integrity and operation of the container. Further, the container must be capable of withstanding the pressure required by the product, must be corrosive-resistant, and must be resistant to physical or chemical changes to the product contained therein that may, for example, form particles clogging the orifice. This is particularly important as the present compositions contain a surfactant and an acid, two components known to increase the potential for corrosion.

The selection of a suitable container for the aerosol product is based on its adaptability to production methods, compatibility with formulation components, ability to sustain the pressure intended for the product, the interest in design and aesthetic appeal on the part of the manufacturer, and cost. Suitable containers may be made of, for example, steel, aluminum, glass, plastic, or mixtures thereof. The containers may further employ one or more protective coatings such as, for example, sodium nitrate, sodium benzoate, ammonium m-nitrobenzoate, morpholine, 2-methyl butynoyl, Expoxol 9-5, sodium n-lauroylsarcosinate, phenolic, epoxy, or vinyl coatings, to enhance the formulation compatibility or safe handling. Any other known aerosol containers and protective coatings are further contemplated as useful in this regard.

The container may also comprise two or more compartments permitting the final composition to be broken up into separate portions that are physically separated until dispensed from the container through the valve assembly.

Known methods for filling aerosol containers with foamable compositions include processes known as cold fill, under the cup, and pressure fill (through the valve). Such methods for filling an aerosol container are well known to those of ordinary skill in the art and may be found in *The Aerosol Handbook* (Wayne E. Dorland, Caldwell, N.J.) and the *Handbook of Aerosol Technology*, (R. E. Krieger, Malabar, Fla.), both of which are incorporated by reference in their entirety.

In the cold filling method, both the product concentrate and the propellant must be cooled to temperatures of −30° to −40° F. The chilled product concentrate is quantitatively metered into an equally cold aerosol container, then the cold, liquefied gas is added. When sufficient propellant has been added, the valve assembly is placed on the container.

In the under the cap filling method, a filling head that forms a tight seal on the container shoulder is utilized. The filling head holds the valve above the container while propellant under pressure is added through the opening in the container.

In the pressure filling method, the product concentrate is quantitatively placed in the container, the valve assembly is placed on the container, and the liquefied gas, under pressure, is metered through the valve stem into the container. Pressure filling is used for most pharmaceutical aerosols.

Valve Assembly

The function of the valve assembly is to permit the expulsion of the contents of the can in the desired form, at the desired rate, and, in the case of metered valves, in the proper amount or dose. Accordingly, the valve assembly must contribute to the form of the product to be emitted. In particular, aerosol foam valves typically have a large-diameter delivery spout to permit the delivery of the foam. Further, the valve assembly permits the aerosol composition to be released from the container either via continuous delivery or as a metered dose.

The materials used in the manufacture of the valve assembly must be inert towards the aerosol formulations that pass therethrough. Among the materials that can be used in the manufacture of the various valve parts are plastic, rubber, aluminum, stainless steel, and mixtures thereof. The usual aerosol valve assembly is composed of the following parts: actuator, stem, gasket, spring, mounting cup, housing, and dip tube. Valves may also be employed that permit emission of product while the container is upright or inverted. All types of valve assemblies known to those of ordinary skill in the art, including spray valves, sliding gasket valves, deflecting gasket valves, and tilt action valves, are contemplated as capable of delivering the present inventive compositions.

Metering valves are designed to deliver specific quantities of a product each time the valve is actuated. Meter valves are usually employed when the formulation is a potent medication or in other instances where a precise dosing is desired. In metered valve systems, an auxiliary valve chamber regulates the amount of material discharged by virtue of its capacity or dimensions.

The valve assembly may further accommodate an attachment to facilitate delivery of the present inventive foamable pharmaceutical compositions.

Dosage

Appropriate dosage levels for any of the herein described active ingredients are well known to those of ordinary skill in the art and are selected to maximize the treatment of the previously described microbial and/or fungal conditions. Dosage levels on the order of about 0.001 mg to about 5,000 mg per kilogram body weight of the active ingredient components are known to be useful in the treatment of the diseases, disorders, and conditions contemplated herein. Typically, this effective amount of the active agent will generally comprise from about 0.001 mg to about 100 mg per kilogram of patient body weight per day. Moreover, it will be understood that this dosage of ingredients can be administered in a single or multiple dosage units to provide the desired therapeutic effect.

If desired, other therapeutic agents can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

The preferred pharmaceutical compositions may be given in a single or multiple doses daily. In a preferred embodiment, the pharmaceutical compositions are given from one to three times daily. Starting with a low dose twice daily and slowly working up to higher doses if needed is a preferred strategy. The amount of pharmaceutically active ingredients that may be combined with the carrier materials to produce a single dosage form will vary depending upon the host treated, the nature of the disease, disorder, or condition, and the nature of the active ingredients.

It is understood, however, that a specific dose level for any particular patient will vary depending upon a variety of factors, including the activity of the specific pharmaceutically active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

The optimal pharmaceutical formulations will be determined by one skilled in the art depending upon considerations such as the particular pharmaceutically active agent combination and the desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the essential lipids.

EXAMPLES

The following examples are offered to illustrate, but not to limit the claimed subject matter.

Example 1

Exemplified Foamable Suspension Gel Containing Benzoyl Peroxide and Clindamycin

This example demonstrates the manufacture of one embodiment of the foamable suspension gels, containing benzoyl peroxide and clindamycin.

Components

| Item # | Ingredient Name | Grade | Trade Name | Manufacturer/Vendor | % w/w |
|---|---|---|---|---|---|
| | | | Benzoyl Peroxide Dispersion | | |
| 1 | Purified Water | USP | Purified Water | — | 4.330 |
| 2 | Poloxamer 188 | USP | Lutrol ® F68 | BASF | 1.000 |

-continued

| Item # | Ingredient Name | Grade | Trade Name | Manufacturer/Vendor | % w/w |
|---|---|---|---|---|---|
| 3 | Anhydrous Citric Acid | USP | Citric acid anhydrous powder EMPROVE ® | Merck | 0.150 |
| 4 | Sodium Citrate dihydrate | USP | Tri-Sodium citrate dihydrate cryst. EMPROVE ® | Merck | 0.350 |
| 5 | Hydrous Benzoyl Peroxide | USP | Luperox ® A75FP/ Benzoyl Peroxide, 75% USP, Remainder Water | Arkema (Atofina) Chemical/Sigma-Aldrich | 6.670 |
| | | | Sub-total (Items 1-5) | | 12.500 |
| | | | 2% Xanthan Gum | | |
| 6 | Purified Water | USP | Purified Water | — | 36.675 |
| 7 | Edetate Disodium | USP | Dissolvine ®, NA2-P | Akzo Nobel | 0.075 |
| 8 | Xanthan Gum | USP | Xantural ® 11K | CP Kelco | 0.750 |
| | | | Sub-total (Items 6-8) | | 37.500 |
| | | | Clindamycin Phosphate Gel | | |
| 9 | Purified Water | USP | Purified Water | — | 48.475 |
| 10 | Clindamycin Phosphate | USP | Clindamycin Phosphate, USP | Abbott Laboratories | 1.250 |
| 11 | Xanthan Gum | USP | Xantural ® 11K | CP Kelco | 0.250 |
| 12 | Edetate Disodium | USP | Dissolvine ®, NA2-P | Akzo Nobel | 0.025 |
| | | | Sub-total (Items 9-12) | | 50.000 |
| | | | Total | | 100.00 |

Final concentrations of components in gel base:

| Ingredients | Example 1 |
|---|---|
| Purified water | 89.48% |
| Citric Acid | 0.12-0.20% |
| tri-Sodium Citrate | 0.30-0.38% |
| Disodium EDTA | 0.10% |
| Poloxamer 188 | 1.00% |
| Clindamycin Phosphate | 1.25% |
| Benzoyl Peroxide | 6.67% |
| Xanthan Gum | 1.00% |
| pH at room temperature | 4.0-5.5 |

Example 2

Exemplified Foamable Suspension Gel Bases Containing Benzoyl Peroxide and Clindamycin

| Ingredients | Example 2A | Example 2B | Example 2C | Example 2D |
|---|---|---|---|---|
| Purified water | 89.48% | 89.48% | 89.48% | 89.48% |
| Citric Acid | 0.12% | 0.15% | 0.18% | 0.20% |
| tri-Sodium Citrate | 0.38% | 0.35% | 0.32% | 0.30% |
| Disodium EDTA | 0.10% | 0.10% | 0.10% | 0.10% |
| Poloxamer 188 | 1.00% | 1.00% | 1.00% | 1.00% |
| Clindamycin Phosphate | 1.25% | 1.25% | 1.25% | 1.25% |
| Benzoyl Peroxide | 6.67% | 6.67% | 6.67% | 6.67% |
| Xanthan Gum | 1.00% | 1.00% | 1.00% | 1.00% |

-continued

| Ingredients | Example 2A | Example 2B | Example 2C | Example 2D |
|---|---|---|---|---|
| pH at room temperature | 4.5-5.5 | 4.5-5.5 | 4.0-5.0 | 4.0-5.0 |

Example 3

Exemplified Foamable Suspension Gel Bases Containing Benzoyl Peroxide and Clindamycin and a Sun Filter

| Ingredients | Example 3A | Example 3B | Example 3C |
|---|---|---|---|
| Purified water | 85.48% | 87.48% | 84.48% |
| Citric Acid | 0.12-0.20% | 0.12-0.20% | 0.12-0.20% |
| tri-Sodium Citrate | 0.30-0.38% | 0.30-0.38% | 0.30-0.38% |
| Disodium EDTA | 0.10% | 0.10% | 0.10% |
| Poloxamer 188 | 1.00% | 1.00% | 1.00% |
| Clindamycin Phosphate | 1.25% | 1.25% | 1.25% |
| Benzoyl Peroxide | 6.67% | 6.67% | 6.67% |
| Xanthan Gum | 1.00% | 1.00% | 1.00% |
| Sunscreen Grade $TiO_2$ (UV absorber) | 4.00 | — | — |
| PEG-25 PABA (UV absorber) | — | 2.00 | — |
| Tinosorb ® M (UV absorber) | — | — | 5.00 |
| pH at room temperature | 4.0-5.5 | 4.0-5.5 | 4.0-5.5 |

The UV absorbing ingredients in Examples 3A, 3B and 3C are the last ingredients added to the foamable suspension gel.

The foamable suspension gels containing one or more sun filters are blended until the UV absorbers are uniformly dispersed throughout the gel.

Example 4

Exemplified Foamable Suspension Gel Bases Containing Benzoyl Peroxide and Clindamycin and a Retinoid

| Ingredients | Example 4A | Example 4B | Example 4C |
|---|---|---|---|
| Purified water | 89.455% | 89.38% | 89.43% |
| Citric Acid | 0.12-0.20% | 0.12-0.20% | 0.12-0.20% |
| tri-Sodium Citrate | 0.30-0.38% | 0.30-0.38% | 0.30-0.38% |
| Disodium EDTA | 0.10% | 0.10% | 0.10% |
| Poloxamer 188 | 1.00% | 1.00% | 1.00% |
| Clindamycin Phosphate | 1.25% | 1.25% | 1.25% |
| Benzoyl Peroxide | 6.67% | 6.67% | 6.67% |
| Xanthan Gum | 1.00% | 1.00% | 1.00% |
| Tretinoin (Retinoid) | 0.025 | 0.10 | 0.05 |

-continued

| Ingredients | Example 4A | Example 4B | Example 4C |
|---|---|---|---|
| pH at room temperature | 4.0-5.5 | 4.0-5.5 | 4.0-5.5 |

The retinoid in Examples 4A, 4B and 4C is the last ingredient added to the foamable suspension gel. The final concentration of retinoid can be between about 0.025% to about 0.10% w/w. The foamable suspension gel additionally containing one or more retinoids as a third active agent are blended until the retinoid is uniformly dispersed throughout the gel.

Examples 5-9

Exemplified Foamable Suspension Gel Bases Containing Benzoyl Peroxide; Benzoyl Peroxide and Sodium Sulfacetamide; Metronidazole and Sodium Sulfacetamide; and Azole Antimicrobial Agent and Salicylic Acid

| | Example Number: | | | | | |
|---|---|---|---|---|---|---|
| | 5 10% Benzoyl Peroxide Foam % w/w | 6 2.5% Benzoyl Peroxide/ 10% Sodium Sulfacetamide Foam % w/w | 7 5% Sulfur/ 10% Sodium Sulfacetamide Foam % w/w | 8a 0.75% Metronidazole/ 10% Sodium Sulfacetamide Foam % w/w | 8b 1% Clotrimazole/ 10% Sodium Sulfacetamide Foam % w/w | 9 2% Miconazole Nitrate/2% Salicylic Acid Foam % w/w |
| Ingredient | | | | | | |
| Water, purified | 84.17 | 62.4 | 82.4 | 86.65 | 85.40 | 93.4 |
| EDTA, Disodium | 0.50 | 0.10 | 0.10 | 0.10 | 0.10 | 0.10 |
| Sodium Phosphate, dibasic/Sodium Phosphate, monobasic | 0 | 0.5 | 0.5 | 0.5 | 0.5 | 0 |
| Citric Acid/Potassium Citrate | 0 | 0 | 0 | 0 | 0 | 0.5 |
| Poloxamer 188 | 1.00 | 1.00 | 1.00 | 1.00 | 1.00 | 1.00 |
| Salicylic Acid | 0 | 0 | 0 | 0 | 0 | 2.00 |
| Sulfur | 0 | 0 | 5.00 | 0 | 0 | 0 |
| Miconazole Nitrate | 0 | 0 | 0 | 0 | 2.00 | 2.00 |
| Metronidazole | 0 | 0 | 0 | 0.75 | 0 | 0 |
| Sodium Sulfacetamide | 0 | 10.00 | 10.00 | 10.00 | 10.00 | 0 |
| Benzoyl Peroxide (10%) Encapsulated | 0 | 25.00 | 0 | 0 | 0 | 0 |
| Benzoyl Peroxide (75%) | 13.33 | 0 | 0 | 0 | 0 | 0 |
| Xanthan Gum | 1.00 | 1.00 | 1.00 | 1.00 | 1.00 | 1.00 |
| Aerosol Base Total | 100.00 | 100.00 | 100.00 | 100.00 | 100.00 | 100.00 |
| pH @ 25° C. | 4 to 5 | 6.8 to 7.5 | 6.8 to 7.5 | 6.8 to 7.5 | 6.5 to 7.5 | 5 to 6.5 |
| Filling Details: | | | | | | |
| Aerosol Base (Above) | 95.00 | 95.00 | 95.00 | 95.00 | 95.00 | 95.00 |
| Hydrocarbon Propellant | 5.00 | 5.00 | 5.00 | 5.00 | 5.00 | 5.00 |
| | 100.00 | 100.00 | 100.00 | 100.00 | 100.00 | 100.00 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An aqueous foamable suspension gel in a pressurized container, comprising:

an aqueous phase comprising water;

a first active agent that is a retinoid which is sparingly soluble to insoluble in water suspended in the aqueous phase;

optionally a second active agent that is clindamycin or a pharmaceutically acceptable salt or ester thereof;

one or more thickening agents in an amount sufficient to result in the foamable suspension gel having a viscosity of from about 1,000 centipoise to about 20,000 centipoise at 25° C.; and an aerosol propellant;

wherein the gel is aqueous, oil-free, and alcohol free, and the gel forms a homogenous foam when dispensed from the pressurized container.

2. The foamable suspension gel of claim 1, wherein the retinoid is selected from the group consisting of vitamin A, retinol (cis or trans), retinal (cis or trans), retinoic acid (cis), tretinoin, hydroxyretroretinol, didehydroretinoic acid, etretinate, retinyl palmitate, β-carotene, tazarotene, acitretin, adapalene, salts thereof, and mixtures thereof.

3. The foamable suspension gel of claim 2, wherein the retinoid is adapalene.

4. The foamable suspension gel of claim 1, wherein the clindamycin or a pharmaceutically acceptable salt or ester thereof is clindamycin phosphate.

5. The foamable suspension gel of claim 1, wherein the gel has a viscosity of about 5,000 centipoise to about 15,000 centipoise at 25° C.

6. The foamable suspension gel of claim 1, wherein the one or more thickening agents are present in an amount up to 5% by weight based on the total weight of the gel.

7. The foamable suspension gel of claim 6, wherein the one or more thickening agents are present in an amount from about 0.1% to about 2% by weight based on the total weight of the gel.

8. The foamable suspension gel of claim 1, wherein the one or more thickening agents includes a hydrocolloid.

9. The foamable suspension gel of claim 8, wherein the thickening agent is selected from the group consisting of agar, alginate, arabinoxylan, carrageenan, carboxymethylcellulose, hydroxypropyl methylcellulose, cellulose, curdlan, gelatin, gellan, β-glucan, guar gum, gum arabic, locust bean gum, pectin, starch, acrylate copolymers, silica, xanthan gum, a carbomer, salts thereof, and mixtures thereof.

10. The foamable suspension gel of claim 9, wherein the thickening agent is xanthan gum.

11. The foamable suspension gel of claim 1, wherein the aerosol propellant is selected from the group consisting of hydrocarbons, chlorofluorocarbons, dimethyl ether, hydrofluorocarbons, compressed gases, and mixtures thereof.

12. The foamable suspension gel of claim 11, wherein the aerosol propellant is a hydrocarbon propellant.

13. The foamable suspension gel of claim 1, wherein the aerosol propellant is present in an amount from about 3% to about 10% by weight based on the total weight of the gel.

14. The foamable suspension gel of claim 1, further comprising a surfactant.

15. The foamable suspension gel of claim 14, wherein the surfactant is selected from the group consisting of polyoxyethylene fatty ethers, polyoxyethylene fatty esters, fatty acids, sulfated fatty acids, phosphated fatty acids, sulfosuccinates, amphoteric surfactants, non-ionic poloxamers, non-ionic meroxapols, aliphatic amines, sorbitan fatty acid esters, pharmaceutically acceptable salts thereof, and mixtures thereof.

16. The foamable suspension gel of claim 15, wherein the surfactant is a polyoxyethylene fatty ether.

17. The foamable suspension gel of claim 1, further comprising a pH-adjusting agent.

18. The foamable suspension gel of claim 1, further comprising a chelating agent.

19. A method of treating acne, the method comprising contacting the skin of an individual in need thereof with the homogenous foam of claim 1.

* * * * *